(12) United States Patent
Alford et al.

(10) Patent No.: US 11,291,370 B2
(45) Date of Patent: *Apr. 5, 2022

(54) DEVICES AND METHODS TO CONVERT CONVENTIONAL IMAGERS INTO LOCK-IN CAMERAS

(71) Applicant: HI LLC, Los Angeles, CA (US)

(72) Inventors: Jamu Alford, Simi Valley, CA (US); Adam Marblestone, Arlington, MA (US)

(73) Assignee: HI LLC, Los Angeles, CA (US)

( * ) Notice: Subject to any disclaimer, the term of this patent is extended or adjusted under 35 U.S.C. 154(b) by 459 days.

This patent is subject to a terminal disclaimer.

(21) Appl. No.: 16/422,906

(22) Filed: May 24, 2019

(65) Prior Publication Data
US 2019/0274548 A1    Sep. 12, 2019

Related U.S. Application Data

(62) Division of application No. 15/988,799, filed on May 24, 2018, now Pat. No. 10,368,752.
(Continued)

(51) Int. Cl.
*A61B 5/00* (2006.01)
*G06T 11/00* (2006.01)
(Continued)

(52) U.S. Cl.
CPC .......... *A61B 5/0077* (2013.01); *A61B 5/0042* (2013.01); *A61B 5/14542* (2013.01);
(Continued)

(58) Field of Classification Search
CPC ............ A61B 5/14553; A61B 2562/04; A61B 2576/026; A61B 5/0042; A61B 5/0066;
(Continued)

(56) References Cited

U.S. PATENT DOCUMENTS

| 3,013,467 A | 12/1961 | Minsky |
| 5,213,105 A | 5/1993 | Gratton et al. |

(Continued)

FOREIGN PATENT DOCUMENTS

| AU | 2009305257 | 5/2014 |
| CN | 102176859 | 1/2014 |

(Continued)

OTHER PUBLICATIONS

Dynamic Interferometry, retrieved Mar. 15, 2018 from https://www.4dtechnology.com/products/dynamic-interferometry/, 3 pages.
(Continued)

*Primary Examiner* — Christopher L Cook
(74) *Attorney, Agent, or Firm* — ALG Intellectual Property, LLC

(57) ABSTRACT

Disclosed herein are devices and methods for modifying a conventional imager to have functional features similar to that of a lock-in camera. Optical mask devices are configured to be coupled to conventional imager sensors and the configuration of the mask devices can be adjusted to acquire image data in rapid succession. One variation of an optical mask device comprises a substrate comprising a pattern of light-blocking and light-transmitting regions and an attachment structure for coupling the optical mask device to the imager. The substrate is configured to adjust the position of the light-blocking regions and light-transmitting regions relative to the light-sensing region of the imager based on a set of one or more predetermined substrate configurations. In some variations, the mask device and/or the imager sensor may be mechanically moved relative to each other based on the set of one or more predetermined substrate configurations.

7 Claims, 9 Drawing Sheets

Related U.S. Application Data

(60) Provisional application No. 62/640,416, filed on Mar. 8, 2018.

(51) Int. Cl.
*G16H 30/40* (2018.01)
*A61B 5/145* (2006.01)
*G06V 10/12* (2022.01)
*G06V 10/88* (2022.01)
*G06V 10/24* (2022.01)

(52) U.S. Cl.
CPC .......... *A61B 5/4064* (2013.01); *G06T 11/005* (2013.01); *G06T 11/008* (2013.01); *G06V 10/12* (2022.01); *G06V 10/242* (2022.01); *G06V 10/88* (2022.01); *G16H 30/40* (2018.01); *A61B 2562/0233* (2013.01); *A61B 2562/046* (2013.01); *A61B 2576/026* (2013.01); *G06T 2200/04* (2013.01); *G06T 2207/10101* (2013.01); *G06T 2207/10136* (2013.01); *G06T 2207/30016* (2013.01); *G06T 2211/412* (2013.01)

(58) Field of Classification Search
CPC ... A61B 5/0071; A61B 5/0084; A61B 5/0097; A61B 5/4064; A61B 5/4875; A61B 5/6803; A61B 5/6868; A61B 8/0808
See application file for complete search history.

(56) References Cited

U.S. PATENT DOCUMENTS

| | | |
|---|---|---|
| 5,625,458 A | 4/1997 | Alfano et al. |
| 5,694,938 A | 12/1997 | Feng et al. |
| 5,856,667 A | 1/1999 | Spirig et al. |
| 6,041,248 A | 3/2000 | Wang |
| 6,091,983 A | 7/2000 | Alfano et al. |
| 6,205,353 B1 | 3/2001 | Alfano et al. |
| 6,334,699 B1 | 1/2002 | Gladnick |
| 6,530,944 B2 | 3/2003 | West et al. |
| 6,738,653 B1 | 5/2004 | Sfez et al. |
| 6,777,659 B1 | 8/2004 | Schwarte |
| 6,825,455 B1 | 11/2004 | Schwarte |
| 6,957,096 B2 | 10/2005 | Sfez et al. |
| 7,053,357 B2 | 5/2006 | Schwarte |
| 7,060,957 B2 | 6/2006 | Lange et al. |
| 7,119,906 B2 | 10/2006 | Pepper et al. |
| 7,144,370 B2 | 12/2006 | Fomitchov |
| 7,429,735 B2 | 9/2008 | Lueerssen et al. |
| 7,498,621 B2 | 3/2009 | Seitz |
| 7,508,505 B2 | 3/2009 | Lustenberger et al. |
| 7,515,948 B1 | 4/2009 | Balberg et al. |
| 7,521,663 B2 | 4/2009 | Wany |
| 7,541,602 B2 | 6/2009 | Metzger et al. |
| 7,560,701 B2 | 7/2009 | Oggier et al. |
| 7,586,077 B2 | 9/2009 | Lehmann et al. |
| 7,595,476 B2 | 9/2009 | Beer et al. |
| 7,620,445 B2 | 11/2009 | Tsujita |
| 7,622,704 B2 | 11/2009 | Wany |
| 7,647,830 B2 | 1/2010 | Sfez et al. |
| 7,671,671 B2 | 3/2010 | Buettgen et al. |
| 7,701,028 B2 | 4/2010 | Alfano et al. |
| 7,706,862 B2 | 4/2010 | Kaufmann et al. |
| 7,733,742 B2 | 6/2010 | Gross et al. |
| 7,747,301 B2 | 6/2010 | Cheng et al. |
| 7,884,310 B2 | 2/2011 | Buettgen |
| 7,889,257 B2 | 2/2011 | Oggier et al. |
| 7,897,928 B2 | 3/2011 | Kaufmann et al. |
| 7,898,649 B2 | 3/2011 | Masumura |
| 7,917,312 B2 | 3/2011 | Wang et al. |
| 7,923,673 B2 | 4/2011 | Buttgen et al. |
| 8,017,858 B2 | 9/2011 | Mann |
| 8,022,345 B1 | 9/2011 | Chang et al. |
| 8,044,999 B2 | 10/2011 | Mullen et al. |
| 8,103,329 B2 | 1/2012 | Fomitchov et al. |
| 8,106,472 B2 | 1/2012 | Kaufmann et al. |
| 8,108,022 B2 | 1/2012 | Balberg et al. |
| 8,115,158 B2 | 2/2012 | Buettgen |
| 8,126,524 B2 | 2/2012 | Balberg et al. |
| 8,143,605 B2 | 3/2012 | Metzger et al. |
| 8,190,245 B2 | 5/2012 | Mitra |
| 8,223,215 B2 | 7/2012 | Oggier et al. |
| 8,280,494 B2 | 10/2012 | Masumura |
| 8,289,502 B2 | 10/2012 | Yoshida |
| 8,299,504 B2 | 10/2012 | Seitz |
| 8,315,483 B2 | 11/2012 | Shuster |
| 8,326,567 B2 | 12/2012 | Masumura |
| 8,336,391 B2 | 12/2012 | Rokni et al. |
| 8,385,691 B2 | 2/2013 | Shuster |
| 8,400,149 B2 | 3/2013 | Stoughton et al. |
| 8,405,823 B2 | 3/2013 | Pfaff |
| 8,423,116 B2 | 4/2013 | Balberg et al. |
| 8,450,674 B2 | 5/2013 | Yang et al. |
| 8,454,512 B2 | 6/2013 | Wang et al. |
| 8,462,355 B2 | 6/2013 | Vucinic et al. |
| 8,525,998 B2 | 9/2013 | Yaqoob et al. |
| 8,554,087 B2 | 10/2013 | Osterberg |
| 8,562,658 B2 | 10/2013 | Shoham et al. |
| 8,644,900 B2 | 2/2014 | Balberg et al. |
| 8,717,574 B2 | 5/2014 | Yang et al. |
| 8,754,939 B2 | 6/2014 | Oggier et al. |
| 8,803,967 B2 | 8/2014 | Oggier et al. |
| 8,817,255 B2 | 8/2014 | Masumura |
| 8,830,573 B2 | 9/2014 | Cui et al. |
| 8,867,798 B2 | 10/2014 | Shuster |
| 8,917,442 B2 | 12/2014 | Baym et al. |
| 8,922,759 B2 | 12/2014 | Gassert et al. |
| 8,954,130 B2 | 2/2015 | Masumura |
| 8,958,622 B2 | 2/2015 | Vija et al. |
| 8,964,028 B2 | 2/2015 | Oggier |
| 8,976,433 B2 | 3/2015 | Masumura |
| 8,997,572 B2 | 4/2015 | Wang et al. |
| 9,000,349 B1 | 4/2015 | Lehmann et al. |
| 9,027,412 B2 | 5/2015 | Rokni et al. |
| 9,046,338 B2 | 6/2015 | Boccara et al. |
| 9,057,695 B2 | 6/2015 | Masumura |
| 9,076,709 B2 | 7/2015 | Felber et al. |
| 9,086,365 B2 | 7/2015 | Wang et al. |
| 9,117,712 B1 | 8/2015 | Oggier et al. |
| 9,131,170 B2 | 9/2015 | Mandelis et al. |
| 9,131,880 B2 | 9/2015 | Balberg et al. |
| 9,140,795 B2 | 9/2015 | Lehmann et al. |
| 9,164,033 B2 | 10/2015 | Edwards et al. |
| 9,195,041 B2 | 11/2015 | Redford |
| 9,200,887 B2 | 12/2015 | Potsaid et al. |
| 9,209,327 B2 | 12/2015 | Neukom et al. |
| 9,226,666 B2 | 1/2016 | Wang et al. |
| 9,232,896 B2 | 1/2016 | Baym et al. |
| 9,234,841 B2 | 1/2016 | Wang et al. |
| 9,237,850 B2 | 1/2016 | Metzger et al. |
| 9,282,931 B2 | 3/2016 | Tearney et al. |
| 9,304,490 B2 | 4/2016 | Masumura |
| 9,313,423 B2 | 4/2016 | Wang et al. |
| 9,329,035 B2 | 5/2016 | Oggier |
| 9,335,154 B2 | 5/2016 | Wax et al. |
| 9,335,605 B2 | 5/2016 | Wang et al. |
| 9,341,715 B2 | 5/2016 | Buettgen et al. |
| 9,351,705 B2 | 5/2016 | Wang et al. |
| 9,435,891 B2 | 9/2016 | Oggier |
| 9,442,196 B2 | 9/2016 | Buettgen et al. |
| 9,466,938 B2 | 10/2016 | Dupret et al. |
| 9,486,128 B1 | 11/2016 | Hannaford et al. |
| 9,488,573 B2 | 11/2016 | Edwards et al. |
| 9,528,966 B2 | 12/2016 | Wang et al. |
| 9,555,444 B2 | 1/2017 | Goodman et al. |
| 9,658,510 B2 | 5/2017 | Kippelen et al. |
| 9,664,606 B2 | 5/2017 | Hajjarian et al. |
| 9,698,196 B2 | 7/2017 | Buettgen et al. |
| 9,730,649 B1 | 8/2017 | Jepsen |
| 2004/0212808 A1 | 10/2004 | Okawa et al. |
| 2005/0219545 A1 | 10/2005 | Chan et al. |
| 2005/0256403 A1 | 11/2005 | Fomitchov |
| 2006/0023621 A1 | 2/2006 | Hwang et al. |

(56) References Cited

U.S. PATENT DOCUMENTS

| | | |
|---|---|---|
| 2006/0122475 A1 | 6/2006 | Balberg et al. |
| 2006/0184042 A1 | 8/2006 | Wang et al. |
| 2006/0184049 A1 | 8/2006 | Tsujita |
| 2006/0187533 A1 | 8/2006 | Nielsen et al. |
| 2006/0224053 A1 | 10/2006 | Black et al. |
| 2006/0247506 A1 | 11/2006 | Balberg et al. |
| 2006/0253007 A1 | 11/2006 | Cheng et al. |
| 2006/0264717 A1 | 11/2006 | Pesach et al. |
| 2006/0274151 A1 | 12/2006 | Lueerssen et al. |
| 2007/0093702 A1 | 4/2007 | Yu et al. |
| 2008/0024767 A1 | 1/2008 | Seitz |
| 2008/0174785 A1 | 7/2008 | Seitz et al. |
| 2008/0219584 A1 | 9/2008 | Mullen et al. |
| 2008/0296514 A1 | 12/2008 | Metzger et al. |
| 2008/0312533 A1 | 12/2008 | Balberg et al. |
| 2009/0066949 A1 | 3/2009 | Masumura |
| 2009/0069674 A1 | 3/2009 | Masumura et al. |
| 2009/0069676 A1 | 3/2009 | Nishihara |
| 2009/0069685 A1 | 3/2009 | Nishihara et al. |
| 2009/0069687 A1 | 3/2009 | Igarashi |
| 2009/0124902 A1 | 5/2009 | Herrmann |
| 2009/0171210 A1 | 7/2009 | Wang |
| 2009/0253989 A1 | 10/2009 | Caplan et al. |
| 2009/0264722 A1 | 10/2009 | Metzger et al. |
| 2010/0000330 A1 | 1/2010 | Rokni et al. |
| 2010/0069750 A1 | 3/2010 | Masumura |
| 2010/0070233 A1 | 3/2010 | Masumura |
| 2010/0073674 A1 | 3/2010 | Yoshida |
| 2010/0152559 A1 | 6/2010 | Cheng et al. |
| 2010/0152591 A1 | 6/2010 | Yu et al. |
| 2010/0285518 A1 | 11/2010 | Viator et al. |
| 2011/0071402 A1 | 3/2011 | Masumura |
| 2011/0101241 A1 | 5/2011 | Cottier et al. |
| 2011/0109962 A1 | 5/2011 | Cui et al. |
| 2011/0117025 A1 | 5/2011 | Dacosta et al. |
| 2011/0172513 A1 | 7/2011 | Nakajima et al. |
| 2011/0228097 A1 | 9/2011 | Motta |
| 2011/0237956 A1 | 9/2011 | Edwards et al. |
| 2011/0249912 A1 | 10/2011 | Shuster |
| 2012/0022381 A1 | 1/2012 | Tearney et al. |
| 2012/0070817 A1 | 3/2012 | Wang et al. |
| 2012/0127557 A1 | 5/2012 | Masumura |
| 2012/0019713 A1 | 8/2012 | McKenna et al. |
| 2012/0275262 A1 | 11/2012 | Song et al. |
| 2013/0107268 A1 | 5/2013 | Boccara et al. |
| 2013/0182096 A1 | 7/2013 | Boccara et al. |
| 2013/0271592 A1 | 10/2013 | Piestun |
| 2014/0176963 A1 | 6/2014 | Kemp |
| 2014/0218748 A1 | 8/2014 | Wax et al. |
| 2015/0238092 A1 | 8/2015 | Masumura |
| 2015/0245771 A1 | 9/2015 | Wang et al. |
| 2015/0320319 A1 | 11/2015 | Alfano et al. |
| 2015/0325973 A1 | 11/2015 | Dupret et al. |
| 2016/0187533 A1 | 6/2016 | Maucec et al. |
| 2016/0235305 A1 | 8/2016 | Wang et al. |
| 2016/0249812 A1 | 9/2016 | Wang et al. |
| 2016/0299218 A1 | 10/2016 | Lehmann |
| 2016/0305914 A1 | 10/2016 | Wang et al. |
| 2017/0038000 A1 | 2/2017 | Fuchsle et al. |
| 2017/0038300 A1 | 2/2017 | Dake et al. |
| 2017/0038459 A1 | 2/2017 | Kubacki et al. |
| 2017/0049326 A1 | 2/2017 | Alfano |
| 2017/0065182 A1 | 3/2017 | Wang et al. |
| 2017/0090018 A1 | 3/2017 | Buettgen et al. |
| 2017/0105636 A1 | 4/2017 | Wang et al. |
| 2017/0122915 A1 | 5/2017 | Vogt et al. |
| 2017/0015682 A1 | 6/2017 | Eom et al. |
| 2017/0161890 A1 | 6/2017 | Chu et al. |
| 2017/0176250 A1 | 6/2017 | Rae et al. |
| 2018/0042480 A1 | 2/2018 | Liu |
| 2018/0016416 A1 | 6/2018 | Nishiwaki et al. |

FOREIGN PATENT DOCUMENTS

| | | |
|---|---|---|
| CN | 104107051 | 10/2014 |
| CN | 104382558 | 3/2015 |
| EP | 1458087 | 10/2005 |
| EP | 1771844 | 4/2007 |
| EP | 2016891 | 1/2009 |
| EP | 2036487 | 3/2009 |
| EP | 2036488 | 3/2009 |
| EP | 2036490 | 3/2009 |
| EP | 2163189 | 3/2010 |
| EP | 1675501 | 9/2013 |
| EP | 1771882 | 9/2013 |
| EP | 2240798 | 8/2016 |
| EP | 2594959 | 1/2017 |
| EP | 2815251 | 3/2017 |
| JP | 2009501581 | 1/2009 |
| WO | 2005025399 | 3/2005 |
| WO | 2006025649 | 3/2006 |
| WO | 2006093666 | 9/2006 |
| WO | 2007035934 | 3/2007 |
| WO | 2008040771 | 4/2008 |
| WO | 2010043851 | 4/2010 |
| WO | 2012080837 | 6/2012 |
| WO | 2012080838 | 6/2012 |
| WO | 2014106823 | 7/2014 |
| WO | 2016138637 | 9/2016 |
| WO | 2016193554 | 12/2016 |

OTHER PUBLICATIONS

HeliCam C3, retrieved on Dec. 6, 2017 on the Internet at http://www.heliotis.ch/html/lockInCameraC3.htm, 2 pages.

Non-Final Office Action received in U.S. Appl. No. 15/988,799 dated Dec. 19, 2018.

Office Action issued by The United States Patent and Trademark Office for U.S. Appl. No. 15/853,538, dated Mar. 12, 2018., 36 pages.

PLOxx PICMA Chip Actuators, retrieved Mar. 15, 2018 from https://www.physikinstrumente.com/en/products/piezoceramic-actuators/linear-actuators/pl0xxpicma-chip-actuators-100800/, 8 pages.

Al-Mujaini, et al., Optical Coherence Tomography: Clinical Applications in Medical Practice, Oman Medical Journal 28(2): 86-91 (2013).

Atlan, et al., Pulsed Acousto-Optic Imaging in Dynamic Scattering Media With Heterodyne Parallel Speckle Detection, Optics Letter 30(11): 1360-1362 (2005).

Blanc, et al., Smart Pixels for Real-time Optical Coherence Tomography, Proceedings of SPIE—The International Society of Optical Engineering, 13 pages (2004).

Broussard, et al., Monitoring Activity in Neural Circuits with Genetically Encoded Indicators, Frontiers in Molecular Neuroscience, vol. 7 (2014).

Choma, et al., Instantaneous quadrature low-coherence interferometry with 3×3 fiber-optic couplers, Optic Letters 28(22): 2003, 2162-2164 (2003).

Franceschini, et al., Cerebral hemodynamics measured by near-infrared spectroscopy at rest and during motor activation, In Proceedings of the Optical Society of America in Vivo Optical Imaging Workshop 2000 (pp. 73-80), Optical Society of America.

Franceschini, et al., Noninvasive Measurement of Neuronal Activity with Near-Infrared Optical Imaging, Neuroimage 21(1): 372-386 (2004).

Giacomelli, et al., Imaging beyond the ballistic limit in coherence imaging using multiply scattered light, Optics express 28:19(5):4268-79 (2011).

Goense, et al., High-resolution of fMRI reveals laminar differences in neurovascular coupling between positive and negative BOLD responses, Neuron 76(3): 629-39 (2012).

Gratton, et al., Dynamic brain imaging: Event-related optical signal (EROS) measures of the time course and localization of cognitive-related activity, Psychonomic Bulletin & Review 5(4): 535-563 (1998).

(56) References Cited

OTHER PUBLICATIONS

Gratton, et al., Fast optical imaging of human brain function, Frontiers in human neuroscience, 4:52 (2010).

Hale, et al., Photorefractive optical lock-in vibration spectral measurement, Applied Optics 36(31): 8248-8258 (1997).

Horinaka, et al., Extraction of quasi-straightforward-propagating photons from diffed light transmitting through a scattering medium by polarization modulation, Optics letters 20(13): 1501-3 (1995).

Horstmeyer, et al., Guidestar-Assisted Wavefront-Shaping Methods for Focusing Light into Biological Tissue, Nature Photonics, vol. 9, No. 9, pp. 563-571 (2015).

Khoury, et al., Photorefractive optical lock-in detector, Optics Letters 16(18): 1442-1444 (1991).

Kim, et al., Biomedical Imaging Applications of Parallel Optical Coherence Tomography and Adaptive Optics, Jeehyum Kim dissertation, The University of Texas at Austin, 168 pages (2004).

Laforest, et al., Co-Integration of a Smart CMOS Image Sensor and a Spatial Light Modulator for Real-Time Optical Phase Modulation, Proc. Of SPIE-IS&T, vol. 2014, 9022:90220N-1 (Mar. 2014).

Lange, et al., Demodulation pixels in CCD and CMOS technologies for time-of-flight ranging, InProc. SPIE 3965: 177-188 (2000).

Leveque, et al., Ultrasonic tagging of photon paths in scattering media: parallel speckle modulation processing, Optics Letters 24(3): 181-3 (1999).

Li, et al., Pulsed Ultrasound-Modulated Optical Tomography Using Spectral-Hole Burning as a Narrowband Spectral Filter, Applied Physics Letters 93(1): 011111 (2008).

Liu, et al., Bit-efficient, sub-millisecond wavefront measurement using a lock-in camera for timereversal based optical focusing inside scattering media, Optics letters 41(7): 1321-4 (2016).

Liu, et al., Lock-in camera based heterodyne holography for ultrasound-modulated optical tomography inside dynamic scattering media, Applied physics letters 108(23): 231106 (2016).

Mahan, et al., Ultrasonic Tagging of Light: Theory, Proceedings of the National Academy of Sciences 95 (24):14015-14019 (1998).

Mao, et al., Optical Lock-In Detection of FRET Using Synthetic and Genetically Encoded Optical Switches, Biophysical Journal, 94: 4515-4524 (2008).

Marriott, et al., Optical lock-in detection imaging microscopy for contrast-enhanced imaging in living cells, PNAS 105(45): 17789-17794 (2008).

Matthews, et al., Deep tissue imaging using spectroscopic analysis of multiply scattered light, Optica. 1(2): 105-111 (2014).

Mohseni, et al., High-performance optical modulators based on stepped quantum wells. In Quantum Sensing and Nanophotonic Devices III, International Society for Optics and Photonics vol. 6127, p. 61270D (2006).

Monte Carlo, et al., eXtreme (MCX), retrieved on Dec. 16, 2017 from http://mcx.sourceforge.net/cgi-bin/index.cgi, 2 pages.

Patwardhan, et al., Quantitative diffuse optical tomography for small animals using an ultrafast gated image intensifier, Journal of Biomedical Optics.13(1): 011009-011009-7 (2008).

Popescu, et al., Optical coherence tomography: fundamental principles, instrumental designs and biomedical applications, Biophys Rev 3: 155-169 (2011).

Powell, et al., Gradient-Based Quantitative Image Reconstruction in Ultrasound-Modulated Optical Tomography: First Harmonic Measurement Type in a Linearized Diffusion Formulation, IEEE Transactions on Medical Imaging 35(2): 456-467 (Feb. 2016).

Puszka, et al., Time-resolved diffuse optical tomography using fast-gated single-photon avalanche diodes, Biomedical optics express, 2013, vol. 4, No. 8, pp. 1351-1365 (Year: 2013).

Qureshi, et al., In Vivo Study of Optical Speckle Decorrelation Time Across Depths in the Mouse Brain, Biomedical Optics Express 8(11): 4855-4864 (2017).

Ruan, et al., Pulsed Ultrasound Modulated Optical Tomography with Harmonic Lock-In Holography Detection, JOSA A 30(7): 1409-1416 (2013).

Sakadzic, et al., High-Resolution Ultrasound-Modulated Optical Tomography in Biological Tissues, Optics Letters 29(23): 2770-2772 (2004).

Schmitt, et al., Use of polarized light to discriminate short-path photons in a multiply scattering medium, Applied optics 31(30): 6535-46 (1992).

Steinbrink, et al., Illuminating the BOLD Signal: Combined fMRI-fNIRS Studies, Magnetic Resonance Imaging 24(4): 495-505 (2006).

Strauss, et al., Synthetic-array heterodyne detection: a single-element detector acts as an array, Optics Letters 19(20): 1609-1611 (1994).

Thrane, et al., Complex decorrelation averaging in optical coherence tomography: a way to reduce the effect of multiple scattering and improve image contrast in a dynamic scattering medium, Opt Lett. 42(14): 2738-2741 (2017).

Tucker-Schwartz, et al., Photothermal optical lock-in optical coherence tomography for in vivo imaging, Biomedical Optics Express 6(6): 2268-2282 (2015).

Van Der Laan, et al., Evolution of circular and linear polarization in scattering environments, Optics express 23(25): 31874-88 (2015).

Wang, et al., Deep-Tissue Focal Fluorescence Imaging with Digitally Time-Reversed Ultrasound-Encoded Light, Nature Communications, vol. 3, Article 928 (Jun. 16, 2012).

Wang, et al., Three dimensional optical angiography, Optics express 15(7): 4083-97 (2007).

Wheaton, et al., Open architecture time of fight 3D SWIR camera operating at 150 MHz modulation frequency, Optics Express 25(16): 19291-7 (2017).

Xu, et al., Time-Reversed Ultrasonically Encoded Optical Focusing into Scattering Media, Nature Photonics 5(3): 154-157 (2011).

520

| Adjusting positions of light-blocking and light transmitting region of an optical mask device at a predetermined number (X) of time points to a plurality of predetermined positions that correspond with a predetermined number of phases of a reference light signal | 522 |

↓

| Acquiring light interference data for each of the plurality of predetermined positions using a detector pixel array of an imager | 524 |

↓

| Calculating a plurality (X) of light intensity values corresponding to the number (X) of phases of the reference light signal, wherein changes in the plurality of light intensity values over time represent neural activity | 526 |

FIG. 5B

DEVICES AND METHODS TO CONVERT CONVENTIONAL IMAGERS INTO LOCK-IN CAMERAS

RELATED APPLICATIONS

The present application is a divisional application of U.S. patent application Ser. No. 15/988,799, filed May 24, 2018, which claims priority under 35 U.S.C. § 119(e) to U.S. Provisional Patent Application No. 62/640,416, filed Mar. 8, 2018. These applications are incorporated herein by reference in their respective entireties.

BACKGROUND

Imaging modalities such as optical coherence tomography (OCT) and ultrasound-modulated optical tomography (UOT) can be used to generate images of a target region in highly-scattering media. For example, OCT and UOT can be used for non-invasive imaging of tissue regions below a skin surface. However, because biological tissue is a highly-scattering medium, the signal-to-noise ratio is fairly poor and limits the resolution of images acquired using OCT or UOT. Changes in the optical properties of the target region that occur during the acquisition time window may result in image blur and/or information loss, for example due to decorrelation of the speckle interference pattern which is to be measured in these techniques. For example, changes in tissue blood perfusion and/or neural activity can occur rapidly, decorrelating or otherwise corrupting UOT or OCT measurements, or other interference based or holographic measurements, if the measurements occur on a slower timescale than the tissue decorrelation.

An imager having a very rapid image data acquisition rate (e.g., frame rate) compared to the decorrelation timescale can help improve the signal quality for OCT or UOT or other interference based or holographic measurement techniques in rapidly decorrelating turbid media. One example of an imager potentially having a sufficiently fast frame rate is a lock-in camera, which is able to acquire multiple measurements of a light field rapidly at each detector pixel in a temporally precise fashion synchronized with an external trigger or oscillation, storing the multiple measurements in multiple electronic charge storage "bins" within each pixel. Phase shifting holography operations using lock-in cameras can help improve the resolution and signal quality of low-coherence interferometry or UOT imaging. However, lock-in camera sensors often lack features that are common in high-performance conventional imager sensors. For example, lock-in camera sensors currently have a lower pixel count and electron well-depth as compared to conventional imager sensors. Other optical arrangements that simulate the rapid data acquisition rate of lock-in cameras in the context of spatially resolved holographic wavefront measurements use two or more imagers with precise pixel-level alignment and matched optical path lengths. One example of such optical arrangement is an imager system comprising a plurality of separate imagers that are optically aligned with each other, such that any given pixel(s) on the imagers have a known one-to-one correspondence with each other (OLIC configuration). However, the use of multiple precisely aligned imagers can be cumbersome and prone to alignment errors. Accordingly, improvements to imagers for high-speed, high pixel-count image data acquisition are desirable.

SUMMARY

Disclosed herein are optical mask devices and methods for modifying a conventional imager to have functional features similar to that of a lock-in camera. For example, the devices and methods described herein may allow a single conventional imager to perform the same phase shifting holography or beat frequency demodulation operations as a 2-bin or 4-bin lock-in camera or an OLIC imager system having two imagers or four imagers, respectively. In one variation, the device may be an optical mask device configured to be coupled to a conventional imager comprising a sensor with a detector pixel array. The optical mask device may comprise a substrate comprising a pattern of light-blocking regions and light-transmitting regions that controls the transmission of light onto particular light-sensing regions of the imager sensor (e.g., to certain set(s) of detector pixels of the imager sensor). The pattern on the substrate may be fixed such that the locations and/or the optical properties (e.g., transmission and/or reflectance of light, etc.) of the light-blocking regions and the light-transmitting regions remains unchanged during an image acquisition window (e.g., exposure time of a single frame of the imager sensor). Alternatively or additionally, the pattern on the substrate may vary (e.g., be tuned or modified) during the image acquisition window such that light data is acquired by different sets of detector pixels of the imager sensor at different times in a manner controlled by the changing substrate pattern. In some variations, the locations and/or the optical properties of the light-blocking and light-transmitting regions relative to a light-sensing region of an imager vary for different mask patterns. In some variations, the optical mask device may be movable relative to the imager sensor and/or the imager sensor may be movable relative to the optical mask device, such that different sets of detector pixels are exposed for the collection of light data at different times in a programmable or controllable fashion. For example, in variations where the mask pattern is static (i.e., unchanging), the imager sensor may be rapidly shifted in position by a predetermined number of pixels (e.g., about 1, 2, 3, 4 or more pixels) during the image acquisition time window. This may "streak" the acquired image data corresponding to a single image point across the predetermined number of pixels such that the light from a single image point is impinged upon multiple detector pixels over time. For example, a single image point may impinge upon distinct detector pixels at different times during one or more imager exposures or frames. The "streak" can be in a linear pattern (e.g., across rows or columns of the detector pixel array) or in a grid pattern.

In OCT and UOT or other holography or interference-based imaging applications, including low-coherence interferometry imaging applications, changing the relative positions of light-blocking (and/or light-transmitting) regions of a mask relative to the light-sensing region of a conventional imager sensor may simulate the function of a lock-in camera for the acquisition of interference patterns or speckle patterns or images. Adjusting the mask configuration (either by changing the mask pattern or changing the relative position of the mask pattern to the imager sensor) to a set of predetermined patterns or predetermined positions in synchrony with phase changes in the reference light signal (and/or ultrasound signal in the case of UOT) may simulate the effect of acquiring speckle image data using a lock-in camera. For example, adjusting the mask configuration to two (or four) predetermined patterns or positions in synchrony with two (or four) phase changes in the reference light signal may acquire speckle image data that approximates the speckle image data acquired by a 2-bin (or 4-bin) lock-in camera.

In some variations, the pattern of an optical mask device may be electrically (e.g., digitally) controlled, and may comprise, for example, a spatial light modulator (SLM), a digital micromirror device (DMD), electrically tunable retro-reflector array or absorber array, and/or other very high-speed patterned electronic shutter. Electrically adjusting the mask pattern can be used instead of, or in addition to, relative motion between the optical mask and the imager. Patterns of light-blocking and light-transmitting regions on an optical mask device, such as the dimensions and locations of pattern features, may be adjusted to match the pixel size and dimensions of conventional imager sensors such that speckle image data may be acquired in the manner of a lock-in camera while retaining desirable features (e.g., high pixel-count, increased electron well depth, etc.) and commercial availability (e.g., high-volume, low-cost components) of conventional imager sensors.

One variation of an optical mask device may comprise a mask substrate comprising an array of optical structures with electrically-tunable optical properties, where the optical properties of the array of optical structures may be adjustable to alter a pattern of light-blocking regions and light-transmitting regions on the mask substrate, and an attachment structure for coupling the mask substrate to an imager such that the mask substrate is disposed over a light-sensing region of the imager. The array of optical structures may be configured to alter the pattern of the light-blocking regions and the light-transmitting regions according to a first predetermined substrate configuration and a second predetermined substrate configuration, where portions of the light-sensing region of the imager are located under the light-transmitting regions of the mask substrate in the first predetermined substrate configuration and are located under the light-blocking regions of the mask substrate in the second predetermined substrate configuration. The light-transmitting region in the first predetermined substrate configuration is a light-blocking region in the second predetermined substrate configuration. The optical structures may comprise one or more of the structures selected from a list consisting of stepped quantum well heterostructures, liquid crystal-based transmission modulators, digital micromirrors, spatial light modulators, and MEMS-based reflectors. The pattern may comprise alternating rows of the light-blocking regions and the light-transmitting regions, and/or may comprise alternating columns of the light-blocking regions and the light-transmitting regions, and/or may comprise a checkerboard arrangement of the light-blocking regions and the light-transmitting regions. The device may further comprise an input port configured to receive a mask substrate configuration signal, where the mask substrate may be configured to alter the pattern at time points indicated by a mask configuration signal. In some variations, the mask substrate configuration signal may comprise a synchronization signal that synchronizes a light source light pulse with a mask substrate configuration change. A light signal of the light source may change phase at each light pulse and the light source may be a light source of an interferometry system that produces an interference pattern in the form of a speckle image. The mask substrate may be configured to transition between the first predetermined substrate configuration to the second predetermined substrate configuration at change of phase of the interference pattern. The light signal phase changes and substrate configuration changes may occur within a speckle decorrelation time interval. The array of optical structures may be configured to alter the pattern according to a third predetermined substrate configuration and a fourth predetermined substrate configuration, where portions of the light-sensing region of the imager located under the light-transmitting regions of the mask substrate in any one of the four predetermined substrate configurations are located under the light-blocking regions of the mask substrate in any one of the other three predetermined substrate configurations. In some variations, the pattern may comprise one or more of the light-transmitting regions having a total area that occupies about 50% of the total area of the mask substrate. In some variations, the pattern comprises one or more of the light-transmitting regions having a total area that occupies about 25% of the total area of the mask substrate.

Also disclosed herein are methods for non-invasive optical detection of neural activity. One variation of a method may comprise adjusting an optical mask device disposed over a light-sensing region of an imager to have a first pattern of light-blocking regions and light-transmitting regions, acquiring a first set of light interference pattern data from brain matter at a first time point using a first set of detector pixels in the light-sensing region of the imager, adjusting the optical mask device to have a second pattern of light-blocking regions and light-transmitting regions, acquiring a second set of light interference data from brain matter at a second time point using a second set of detector pixels in the light-sensing region of the imager, and calculating a first light intensity value by combining intensity values of each detector pixel in the first set of detector pixels and calculating a second light intensity value by combining intensity values of each detector pixel in the second set of detector pixels. The detector pixels in the second set may be different from the detector pixels in the first set. The first light interference pattern data may comprise a combination of a first reference light signal having a first phase and a first sample light signal from a target voxel in the brain matter, and the second light interference pattern data may comprise a combination of a second reference light signal having a second phase and a second sample light signal from the target voxel. For example, the first phase may be 0 and the second phase may be $\pi$. In some variations, the method may further comprise adjusting the optical mask to have a third pattern of light-blocking regions and light-transmitting regions, acquiring a third set of light interference data from brain matter at a third time point using a third set of detector pixels in the light-sensing region of the imager, where the third light interference pattern data comprises a combination of a third reference light signal having a third phase and a third sample signal from the target voxel, adjusting the optical mask to have a fourth pattern of light-blocking regions and light-transmitting regions, acquiring a fourth set of light interference data from brain matter at a fourth time point using a fourth set of detector pixels in the light-sensing region of the imager, where the fourth light interference pattern data comprises a combination of a fourth reference light signal having a fourth phase and a fourth sample signal from the target voxel, and calculating a third light intensity value by combining intensity values of each detector pixel in the third set of detector pixels and calculating a fourth light intensity value by combining intensity values of each detector pixel in the fourth set of detector pixels. The first phase may be 0, the second phase may be $\pi/2$, the third phase may be $\pi$, and the fourth phase may be $3\pi/2$. The method may further comprise determining a physiological optical parameter of the target voxel based on the first, second, third, and fourth light intensity values.

Optionally, some methods may comprise determining a physiological optical parameter of the target voxel based on the first and second light intensity values. The physiological optical parameter may be the level of deoxygenated and/or oxygenated hemoglobin concentration of relative abundance, and/or the physiological optical parameter is the level of neuronal movement or activity of brain matter. In some variations, the first and second sample light signals may each be frequency encoded, and/or the first and second sample light signals may be frequency encoded using ultrasound pulses delivered to the target voxel. Alternatively or additionally, the first and second sample light signals may each be path length encoded.

One variation of a method for non-invasive optical measurement of neural activity may comprise adjusting positions of light-blocking and light-transmitting regions of an optical mask at a predetermined number (X) of time points to a plurality of predetermined positions that correspond with a predetermined number (X) of phases of a sample light signal, wherein the optical mask is disposed over a detector pixel array of an imager, acquiring light interference data for each of the plurality of predetermined positions using the detector pixel array, and calculating a plurality (X) of light intensity values corresponding to the number (N) of phases of the sample light signal by averaging imager detector pixel values for each of the predetermined number (X) of time points, where changes in the plurality of light intensity values over time represent neural activity.

One variation of an optical mask device may comprise a mask substrate that comprises an array of optical structures with electrically-tunable optical properties and a pattern of light-blocking regions and light-transmitting regions and an attachment structure for coupling the optical mask to an imager such that the mask substrate is disposed over a light-sensing region of the imager. The optical properties of the optical structures may be adjustable to alter the pattern of the light-blocking and the light-transmitting regions and may be configured to alter the pattern of the light-blocking regions and light-transmitting regions according to a first predetermined substrate configuration and a second predetermined substrate configuration. Portions of the light-sensing region of the imager located under light-transmitting regions of the mask substrate in the first substrate configuration may be located under light-blocking regions of the mask substrate in the second substrate configuration. For example, a light-transmitting region in the first predetermined substrate configuration may be a light-blocking region in the second predetermined substrate configuration. The optical structures may comprise one or more of the structures selected from a list consisting of stepped quantum well heterostructures, liquid crystal-based transmission modulators, digital micromirrors, spatial light modulators, and MEMS-based reflectors. In some variations, the pattern may comprise alternating rows of light-blocking regions and light-transmitting regions, or the pattern may comprise alternating columns of light-blocking regions and light-transmitting regions, or the pattern may comprise a checkerboard arrangement of light-blocking regions and light-transmitting regions. Alternatively or additionally, the pattern may comprise one or more light-transmitting regions having a total area that occupies about 50% of the total area of a substrate, or may comprise one or more light-transmitting regions having a total area that occupies about 25% of the total area of a substrate. A mask device may further comprise an input port configured to receive a mask substrate configuration signal, where the mask substrate may be configured to alter the pattern at time points indicated by the mask configuration signal. The mask substrate configuration signal may comprise a synchronization signal that synchronizes a light source pulse with a mask substrate configuration change. A light signal of the light source may change phase at each pulse and the light source may be a light source of an interferometry system that produces an interference pattern in the form of a speckle image or pattern, and the substrate may be configured to transition between the first predetermined substrate configuration to the second predetermined substrate configuration at each light signal phase change. Examples of interferometry systems that may comprise an imager and any of the mask devices described herein may include, but are not limited to, low-coherence interferometry systems, optical coherence tomography systems (e.g., swept-source OCT), and ultrasound-modulated optical tomography. In some variations, the light signal phase changes and substrate configuration changes may occur within a speckle decorrelation time interval. The mask substrate may comprise a third predetermined substrate configuration and a fourth predetermined substrate configuration, where portions of the light-sensing region of the imager located under light-transmitting regions of the mask substrate in any one of the four predetermined substrate configurations are located under light-blocking regions of the mask substrate in any one of the other three predetermined substrate configurations.

Another variation of an optical mask device may comprise a mask substrate comprising an actuator configured to move the light-sensing region of the imager with respect to the substrate and a pattern of light-blocking regions and light-transmitting regions, and an attachment structure for coupling the optical mask to an imager such that the substrate is disposed over a light-sensing region of the imager. The actuator may be configured to move the mask substrate between a first predetermined substrate configuration and a second predetermined substrate configuration, where the mask substrate is at a first location with respect to the light-sensing region of the imager when in the first substrate configuration and the mask substrate is at a second location with respect to the light-sensing region of the imager when in the second substrate configuration. Portions of the light-sensing region of the imager located under light-transmitting regions of the substrate in the first substrate configuration may be located under light-blocking regions of the substrate in the second substrate configuration. Optionally, the device may further comprise an actuator configured to move the light-sensing region of the imager with respect to the mask substrate. The actuator may be a piezo actuator, and may be configured to move the substrate from about 2 µm to about 10 µm relative to the light-sensing region of the imager. The device may also comprise a substrate position sensor. In some variations, the pattern may comprise alternating rows of light-blocking regions and light-transmitting regions, or the pattern may comprise alternating columns of light-blocking regions and light-transmitting regions, or the pattern may comprise a checkerboard arrangement of light-blocking regions and light-transmitting regions. Alternatively or additionally, the pattern may comprise one or more light-transmitting regions having a total area that occupies about 50% of the total area of a substrate, or may comprise one or more light-transmitting regions having a total area that occupies about 25% of the total area of a substrate. A mask device may further comprise an input port configured to receive a mask substrate configuration signal, where the mask substrate may be configured to alter the pattern at time points indicated by the mask configuration signal. The mask substrate configuration signal may comprise a synchronization signal that synchronizes a light source pulse with a mask substrate configuration change. A light signal of the light source may change phase at each pulse and the light source may be a light source of a low-interferometry system that produces an interference pattern in the form of a speckle image, and the substrate may be configured to transition between the first predetermined substrate configuration to the second predetermined substrate configuration at each light signal phase change. In some variations, the light signal phase changes and substrate configuration changes may occur within a speckle decorrelation time interval. The mask substrate may comprise a third predetermined substrate configuration and a fourth predetermined substrate configuration, where portions of the light-sensing region of the imager located under light-transmitting regions of the mask substrate in any one of the four predetermined substrate configurations are located under light-blocking regions of the mask substrate in any one of the other three predetermined substrate configurations.

Also disclosed herein are methods for non-invasive optical detection of neural activity. One variation of a method for non-invasive optical detection of neural activity may comprise adjusting an optical mask device disposed over a light-sensing region of an imager to have a first pattern of light-blocking regions and light-transmitting regions, acquiring a first set of light interference pattern data from brain matter at a first time point using a first set of detector pixels in the light-sensing region of the imager, adjusting the optical mask device to have a second pattern of light-blocking regions and light-transmitting regions, acquiring a second set of light interference data from brain matter at a second time point using a second set of detector pixels in the light-sensing region of the imager, and calculating a first light intensity value by averaging combining intensity values over the first set of detector pixels and calculating a second light intensity value by averaging combining intensity values over the second set of detector pixels. The detector pixels in the second set may be different from the detector pixels in the first set. The first light interference pattern may comprise a combination of a first reference light signal having a first phase and a first sample light signal from a target voxel in the brain matter and the second light interference pattern may comprise a combination of a second reference light signal having a second phase and a second sample signal from the target voxel. The first phase may be 0 and the second phase may be $\pi$. The method may further comprise determining a physiological optical parameter of the target voxel based on the first and second light intensity values. The physiological optical parameter may be the level of deoxygenated and/or oxygenated hemoglobin concentration of relative abundance, or the level of neuronal movement or activity of brain matter. In some variations, the first and second sample light signals may each frequency encoded. For example, the first and second sample light signals may be frequency encoded using ultrasound pulses delivered to the target voxel. In some variations, the first and second sample light signals may each path length encoded. The method may further comprise adjusting the optical mask to have a third pattern of light-blocking regions and light-transmitting regions, acquiring a third set of light interference data from brain matter at a third time point using a third set of detector pixels in the light-sensing region of the imager, where the third light interference pattern may comprise a combination of a third reference light signal having a third phase and a third sample signal from the target voxel, adjusting the optical mask to have a fourth pattern of light-blocking regions and light-transmitting regions, acquiring a fourth set of light interference data from brain matter at a fourth time point using a fourth set of detector pixels in the light-sensing region of the imager, where the fourth light interference pattern may comprise a combination of a fourth reference light signal having a fourth phase and a fourth sample signal from the target voxel, and calculating a third light intensity value by combining intensity values over the third set of detector pixels and calculating a fourth light intensity value by combining intensity values over the fourth set of detector pixels. The first phase may be 0, the second phase may be $\pi/2$, the third phase may be $\pi$, and the fourth phase may be $3\pi/2$, and in some variations, the method may further comprise determining a physiological optical parameter of the target voxel based on the first, second, third, and fourth light intensity values.

In one variation, a method for non-invasive optical measurement of neural activity may comprise adjusting positions of light-blocking and light-transmitting regions of an optical mask at a predetermined number (X) of time points to a plurality of predetermined positions that correspond with a predetermined number (X) of phases of a sample light signal, where the optical mask is disposed over a detector pixel array of an imager, acquiring light interference data for each of the plurality of predetermined positions using the detector pixel array, and calculating a plurality (X) of light intensity values corresponding to the number (N) of phases of the sample light signal by averaging imager detector pixel values for each of the predetermined number (X) of time points, where changes in the plurality of light intensity values over time represent neural activity.

BRIEF DESCRIPTION OF THE DRAWINGS

FIG. 5B is a flowchart depiction of one variation of a method for non-invasive optical detection of neural activity.

DETAILED DESCRIPTION

Figure 1A:
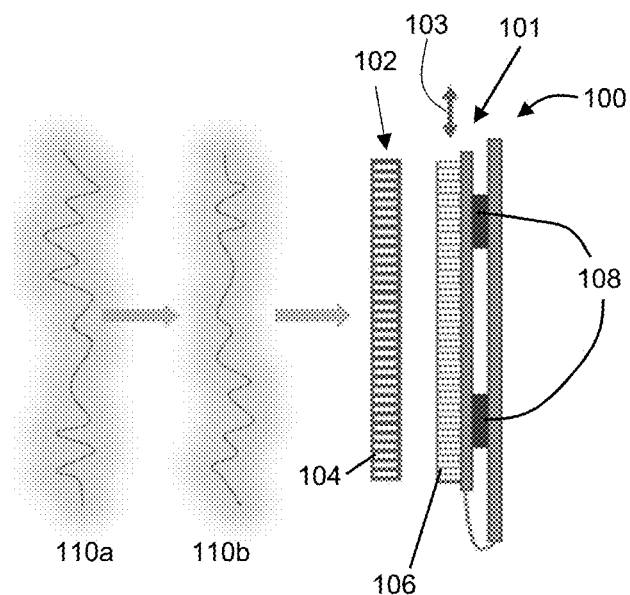
FIG. 1A is a schematic depiction of one variation of an imaging assembly comprising an optical mask device.

Described herein are optical mask devices configured to be coupled to and disposed over conventional imager sensors and methods of adjusting the configuration of the mask devices to acquire image data in rapid succession. Methods may comprise adjusting the configuration of a mask device and acquiring multiple sets of image data (e.g., of interference patterns or speckle images) in synchrony with an external trigger at predetermined acquisition time points. The mask may have a particular mask configuration for each predetermined acquisition time point, and the set of detector pixels that are located in the light-transmitting regions of the mask may acquire a set of detector pixel data at that acquisition time point. The different sets of data acquired by different set of detector pixels at the different acquisition time points may be analogous to image data collected in multiple electronic charge storage "bins" of the detector pixels in a lock-in camera. By adjusting the mask configuration at each data acquisition time point, a conventional imager may be configured to rapidly capture and store multiple sequential samples of image data, with sample-to-sample latencies shorter than readout times of conventional imagers. The devices and methods described herein may be used, for example, to create a 2-bin, 4-bin or any other number of temporally separated bins of image data measurements for each speckle by impinging the light from the speckle on different imager pixels or combinations of pixels at different times.

An imager may be any assembly or system comprising an imager sensor that records light data that may be used to generate an image. An imager sensor may comprise an array of charged coupled device (CCD) or complementary metal-oxide semiconductor (CMOS) units or detector pixels. A conventional imager is one in which each detector pixel acquires and retains light data for a moment in time. Successive light measurements by a detector pixel "overwrites" the previous light measurement in that detector pixel. Optionally, an imager may comprise one or more optical components disposed over the imager sensor. Optical components may include one or more of a transparent window, a lens (e.g., objective lens, relay lens, etc.), a filter (e.g., polarizing filter, wavelength or color filter, mosaic filter, neutral density filter, etc.), a prism, a condenser, a shutter (e.g., a variable aperture component), and the like. Examples of imagers may include, but are not limited to, line scan cameras, CCD arrays, CMOS arrays, sCMOS arrays, EM-CCD arrays, photodiode arrays, avalanche diode arrays, extended well depth cameras, wrap-around cameras, CMOS smart pixel devices or other types of imagers.

An interferometry system (e.g., OCT, low-coherence interferometry, UOT) may comprise a light source and a beam splitter that directs a portion of the light beam (i.e., sample light) to the tissue sample of an anatomical structure (e.g., the anatomical structure is this case may be the intact head of a patient, including the scalp, skull, and brain, with the tissue voxel comprising brain tissue), while directing another portion of the light beam along a variable (but known) light path (i.e., reference light). The sample light interacts with the tissue sample, and the sample light that interacts with a target tissue region such as a target tissue voxel of brain matter (i.e., signal light) in combination with sample light that interacts with surrounding tissue regions (i.e., background light) may produce a sample light pattern that is directed or emitted back away from the tissue sample. The sample light pattern may then be combined with the reference light to create an interference light pattern (e.g., a speckle image) that selects sample photons that have a path length that is the same as, or similar to, the path length of the reference light. A UOT system may comprise an interferometry system as described above as well as an acoustic assembly configured for delivering ultrasound (e.g., focused ultrasound pulses) into the target tissue region or target voxel. The ultrasound pulse may shift the frequency of the sample light at the target tissue region by the ultrasound frequency (i.e., "tagging" the sample light). The focused ultrasound pulse may have little or no impact on the photons of the background light (i.e., "untagged" background light). The reference light may also be frequency-shifted by the ultrasound frequency so that combining the reference light and the sample light pattern creates an interference pattern that selects sample photons that have the same frequency shift (i.e., selecting tagged photons). When low-coherence interferometry or UOT modalities are used for non-invasive imaging of brain matter below the skin surface and/or below the skull (or any target region in a highly-scattering medium), the reference light signal may cycle through a plurality of preselected or predetermined phase shifts to generate a plurality of interference or speckle patterns from combining sample light emerging from the brain matter (or scattering medium) and the phase-shifted reference light signal. The reference light may step through these phase shifts rapidly, for example, faster than a speckle decorrelation time interval of about 1 ms or less, about 100 µs or less, depending on the imaging depth in tissue, etc., which may be faster than the acquisition or frame rate of conventional imager sensors. The speckle decorrelation time is the time interval beyond which speckle data becomes uncorrelated. When the time interval between successive measurements is greater than or equal to the speckle decorrelation time, then the random phase offset and/or background will change between the successive measurements, which may corrupt the measurement such that the calculation of the intensity or amplitude of the quasi-ballistic photon fraction is no longer possible and/or accurate. The speckle decorrelation time may vary depending on the optical properties of the tissue and/or the selected imaging depth within the tissue, and may be, for example, less than 1 millisecond for imaging more than 3 mm deep into living brain tissue, and/or less than 100 microseconds for imaging through the skull and into the cortical brain tissue underneath). The speckle decorrelation time for a particular interferometry system may be measured using a lock-in camera and/or any of the mask devices described herein disposed over an imager. Lock-in cameras may be configured to measure these rapidly-changing interference patterns or speckle images by measuring each speckle of the speckle image at time points that correspond with the timing of each of the phase shifts and storing that data in a pixel data storage bin. The imaging systems described herein may be configured to measure the interference patterns at each phase shift time point by changing the mask configuration to a pattern that corresponds to that time point, and measuring each speckle of the speckle image using one or more detector pixels that correspond to that time point or phase shift. The speckle image data is stored in a plurality of detector pixels that correspond with that time point or phase shift, as opposed to being stored in a particular data bin of a pixel of a lock-in camera.

In some variations, an imaging system comprising an optical mask device and a conventional imager sensor may be used to measure a time-varying/modulated intensity of the light in each speckle at different time-points in the manner of heterodyne detection, e.g., in order to selectively extract the AC component from a DC background. Individual different pixels and/or combinations of (e.g., neighboring) detector pixels on a conventional imager sensor may be used to sense and store these distinct measurements. In contrast, a lock-in camera may use different electronic data bins of the same photodetector pixel to store these distinct measurements, and an OLIC system may use two or more pixel-by-pixel aligned imagers to achieve a similar effect by recording multiple interferences for the same speckle in a single snapshot on the corresponding aligned pixels of the multiple imagers. Adjusting the optical mask device in a time-varying manner may direct light from each speckle to the imager sensor detector pixel(s) corresponding to each time point cause, causing the detector pixel(s) of the imager sensor to store different time points of the interference pattern at a given speckle. Adjusting the optical mask device may comprise changing the pattern of light-transmitting and light-blocking regions and/or changing the position of the light-transmitting and light-blocking regions of the mask by adjusting the alignment between the imager sensor and the mask over time (e.g., at each time point).

While the devices and methods described herein are explained in the context of low-coherence interferometry and UOT, it should be understood these devices and methods may be used in any imaging context where rapid acquisition of image data at precise or predetermined time points or intervals, and/or in synchrony with an external trigger signal is desired (e.g., in any imaging context where a lock-in camera is used). The devices and methods described herein may be used to detect light modulated (e.g., via amplitude or phase modulation) by other mechanisms, for instance via an external modulator applied before light enters the sample. For example, the devices and methods described herein may be used to measure phase shifts in the modulation of light, which may be used to calculate average time-of-flight variations from a light source to a detector located on the surface of the brain. This can be used to measure fast changes in the optical scattering properties of the brain matter between light source and detector, which may be indicative of fast changes in neural activity (similar to the use of frequency domain diffuse optical tomography). The device and methods described herein may be used for measuring changes in speckle patterns as a function of time, independent of locking to a particular modulation frequency. Examples may include measuring phase-shifted holograms, and/or measuring modulations or oscillations at a particular beat frequency, and/or measuring changes in a speckle pattern (e.g., to calculate the speckle decorrelation interval) that occur faster than the frame rate of a conventional imager. These measurements may be made with or without a reference light signal, light signal phase shifts, ultrasonic modulation, or optoacoustic modulation. In addition, this approach may be used to detect externally modulated light for the purpose of multiplexing light signals from many sources, which each light signal may be modulated differently.

Figure 1B:
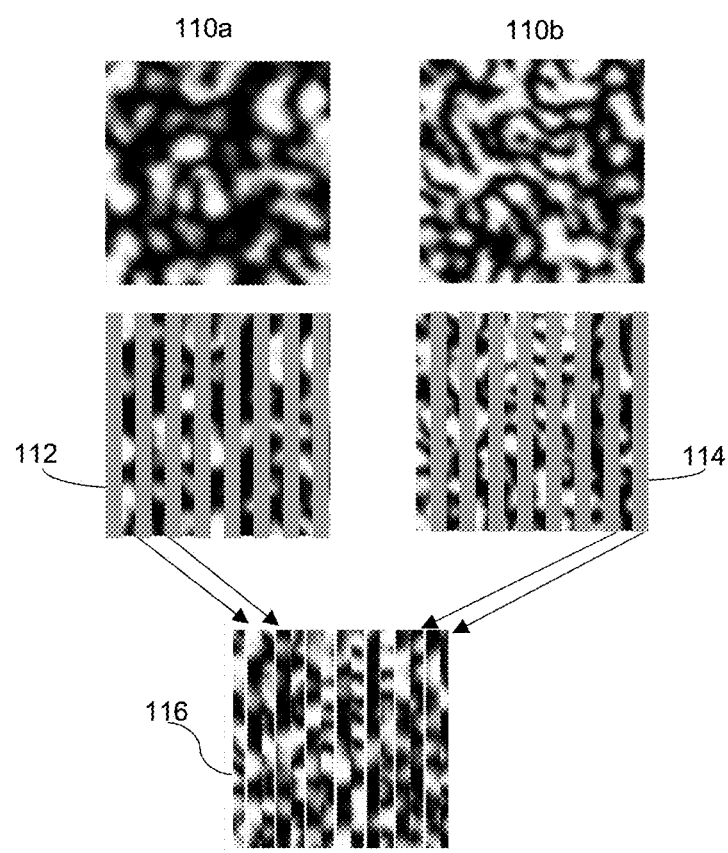
FIG. 1B is a conceptual depiction of an image acquisition method using the imaging assembly of FIG. 1A.

FIG. 1A is a schematic depiction of an imaging system (100) comprising an imager (101) having an imager sensor (106) and an optical mask device (102) disposed over the imager sensor and FIG. 1B depicts examples of speckle image data acquired by the system of FIG. 1A. The imaging system (100) may comprise an optical mask device (102) comprising a mask substrate (104), and an imager comprising an imager sensor (106) comprising an array of detector pixels. In this variation, the imager sensor (106) may be coupled to one or more actuators (108) that are configured to position the imager sensor (106) relative to the optical mask device (102) along the arrow (103) and the optical mask device (102) may be stationary. Alternatively or additionally, the optical mask device (102) may be coupled to one or more actuators that are configured to move the mask device relative to the imager sensor (106). The left side of FIG. 1A represents two interference patterns (110a, 110b) or speckle images that may be measured by a single frame of the imager sensor (106). The pattern on the mask substrate (104) may comprise a series of light-transmitting stripes alternating with a series of light-blocking stripes, which may be vertical as depicted in FIG. 1B or may be horizontal, though other orientations (e.g., stripes at any angle between 0° and 90°, stripes at about 30°, stripes at about 45°, etc.) may be possible. The two different speckle images (e.g., produced by interferometry at different reference beam phase shifts, or otherwise) may be captured on alternating columns of the imager sensor (106). The first and second speckle patterns may be mapped to alternating odd and even columns of the imager sensor by moving the optical mask (102) relative to the imager sensor (106) and/or moving the sensor (106) relative to the optical mask (102) and/or changing the pattern on the mask substrate (104) such that the stripes of light-blocking and light-transmitting regions are flipped. A mask configuration describes the relative locations of the light-transmitting region(s) and the light-blocking region(s) of a mask substrate relative to an imager sensor, including, but not limited to, the location of the optical mask device and/or mask substrate relative to the imager sensor, and/or changes in the optical characteristics of mask substrate regions such that the arrangement or pattern of light-transmitting and light-blocking regions changes on the mask substrate. The optical mask device (102) may be adjusted to the first mask configuration (112) to detect the first speckle image (110a) and the optical mask may be adjusted to the second mask configuration (114) to detect the second speckle image (110b). The overall image detected by the imager sensor (106) is represented by the composite image (116), where the detector pixel data in the odd columns pertain to the first speckle pattern and the detector pixel data in the even columns pertain to the second speckle pattern. As depicted in the composite image (116), each speckle image may undergo a signal loss of about 50% due to the mask pattern where about half the pattern comprises light-blocking regions. In the context of non-invasive brain imaging, the variation in interference or speckle patterns may be due to physiological changes in the brain, such fast changes in optical scattering properties in the brain induced by ultrasound or other modulation, and/or holographic phase shifting of a reference beam, for example. The mask configuration may change from the first configuration to the second configuration within a speckle decorrelation time interval (e.g., about 1 ms or less, 100 µs or less).

In the case of UOT, the difference between the two speckle or interference patterns may be an indicator of the amount of ultrasonically tagged light. In the case of low-coherence interferometry, the difference between the two speckle patterns may represent the differentiation of short-path and long-path wavefronts by isolating interference terms due to path-length-selected photons. The number of speckle patterns measured during an acquisition time window (e.g., less than or equal to the acquisition time for a frame of data of the imager sensor, less than a speckle decorrelation time interval, from about 5 µs to about 100 µs, about 10 µs, about 20 µs, about 40 µs, about 50 µs, about 100 µs, from about 500 µs to about 1 ms, about 800 µs, about 1 ms, etc.) may be determined at least in part by the number of mask configuration changes in the acquisition time window and the pattern of light-transmitting and light-blocking regions for each of those mask configurations. For example, to measure 10 speckle images at 10 acquisition time points within an acquisition time window, the optical mask may have 10 mask patterns where the light-transmitting region in each pattern makes up about a tenth of the area of the substrate. For example, if the mask substrate were divided into columns or vertical stripes, every tenth column or stripe would correspond to a particular interference or speckle pattern. The mask may step through each of the 10 patterns or configurations during the acquisition window (i.e., one pattern per time point), resulting in a composite image where a tenth of the detector pixel data pertains to one interference or speckle pattern.

Devices and Systems

Figure 2A:
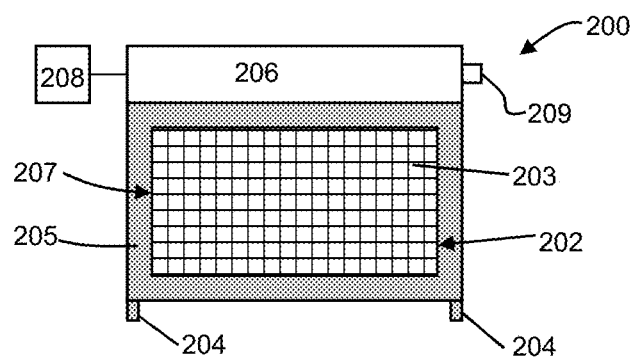
FIG. 2A is a schematic depiction of one variation of an optical mask device.

FIG. 2A depicts one variation of an optical mask device (200) comprising a mask substrate (202) having a substrate pattern comprising an arrangement of light-blocking and light-transmitting regions on the mask substrate (which may also be referred to as a substrate) and one or more attachment structures (204) configured to couple the mask device (200) to an imager. The substrate (202) may comprise an array of optical structures (203). In some variations, the optical properties of the optical structures (203) may be electrically-tunable to form a desired substrate pattern of light-blocking and light-transmitting regions. Alternatively, the optical properties of the optical structures (203) may be fixed in a specific pattern of light-blocking regions and light-transmitting regions. An attachment structure may comprise a frame structure or support structure (205) comprising a central opening (207). The mask substrate (202) may be attached to the support structure (205), for example, by coupling the outer perimeter of the mask substrate (202) to the portions of the support structure (205) around the perimeter of the central opening, such that the substrate pattern (203) is located within the central opening (207). The mask substrate (202) may be configured to alter the pattern of the light-blocking and light-transmitting regions according to one or more predetermined mask substrate configurations. A mask substrate configuration may comprise a particular substrate pattern and/or a particular position of the substrate (or optical mask device) and/or particular positions of the light-transmitting regions and/or light-blocking regions relative to the imager sensor (i.e., light-sensing region of the imager). The patterns of light-transmitting and light-blocking regions of different predetermined substrate configurations may be selected such that a light-transmitting region in one configuration is a light-blocking region in the other configurations. Alternatively or additionally, the position or location of the mask substrate relative to the light-sensing region of the imager to which the optical mask device is attached may be varied according to the predetermined substrate configurations. More generally, the substrate patterns or positions of the light-transmitting regions and the light-blocking regions of the mask substrate relative to the light-sensing region of the imager may be such that portions of the light-sensing region of the imager located under the light-transmitting regions of the mask substrate in one predetermined mask substrate configuration are located under the light-blocking regions of the mask substrate in the other mask substrate configurations. That is, every detector pixel of an imager sensor is exposed to incident light in one mask substrate configuration or substrate pattern, and is blocked from incident light the remaining mask substrate configurations or substrate patterns. In some variations, the optical mask device (200) may comprise electrical circuitry (206) comprising interface electronics configured to send and receive signals from the imager and/or imaging system controller (examples of which are described below and depicted in FIGS. 3A-3B). The electrical circuitry (206) may comprise, for example, an input port (209) that receives mask substrate configuration data or commands, synchronization or trigger signals that regulate the timing of mask substrate configuration changes, and the like. In some variations, the mask substrate (202) may comprise one more actuators (e.g., piezo actuators) configured to move the mask device relative to the imager to which the mask device is attached. The one or more actuators may be in communication with the electrical circuitry (206) so that motion commands from the imaging system controller may be used to control the operation of the one or more actuators. Optionally, the optical mask device (200) may comprise a position sensor (208) in communication with the electrical circuitry (206), and mask substrate position data may be transmitted to the imaging system controller. The system controller may adjust the operation of the one or more actuators based on the data from the position sensor (208) (e.g., position sensor data may be used as a feedback signal to confirm that the one or more actuators are functioning properly). Any of the optical mask devices described herein may be manufactured, and/or packaged, and/or sold as an individual component, separate from any imaging system or assembly. Alternatively or additionally, and of the optical mask devices described herein may be manufactured, and/or packaged, and/or sold in conjunction with an imager sensor. The optical mask devices described herein may be used with an existing interferometry system (e.g., low-coherence interferometry system, OCT, UOT) and/or any imaging system.

In some variations, attachment structures may comprise snap-fit mechanisms, screw-fit mechanisms, adhesive mechanisms, and the like. In some variations, the mask substrate may be attached directly to the imager sensor to from an imager assembly, which may be enclosed in a single housing. An imager assembly comprising an optical mask device and an imager sensor may be included in any imaging system, such as an interferometry system for non-invasive brain imaging. In some variations, the mask substrate may not physically touch the imager sensor but may be aligned with the imager sensor through a mechanical coupling structure, such as any of the attachment structures described above, that allows for independent alignment and or calibration. The optical mask device may be attached to the imager sensor during the manufacturing process of an imager assembly. Alternatively or additionally, the optical mask device may be attached to an existing imager sensor (e.g., as an after-market modification).

Figure 2B:
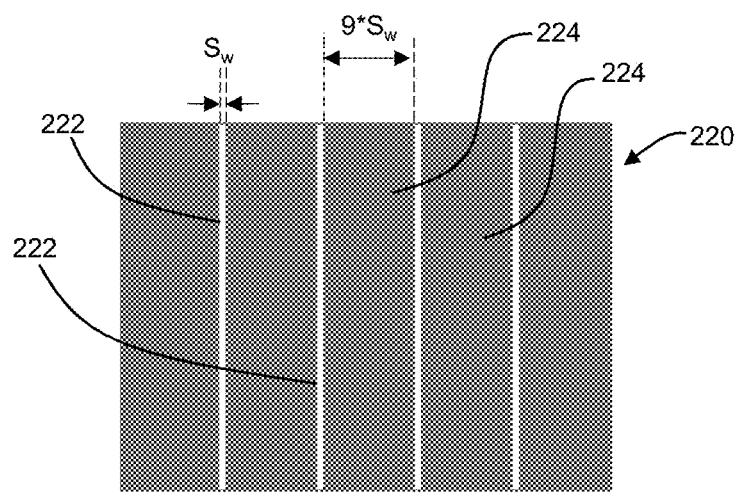
FIG. 2B depicts one variation of a mask substrate pattern.
Figure 2C:
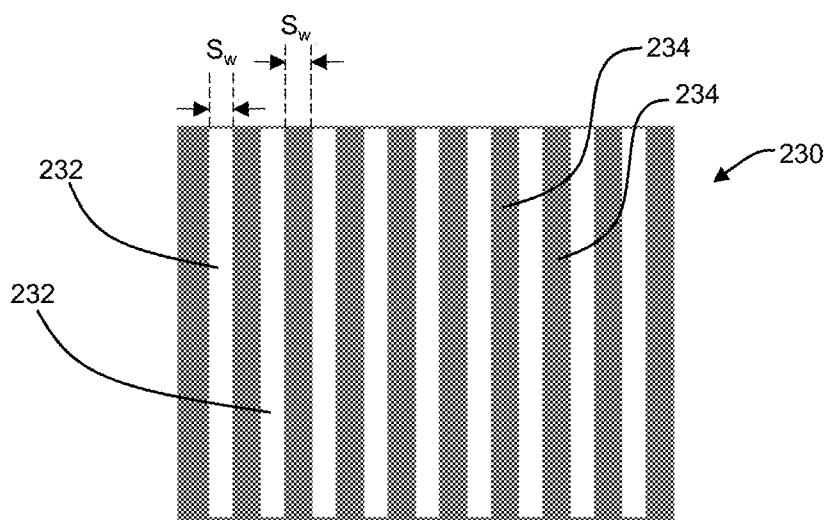
FIG. 2C depicts another variation of a mask substrate pattern.

A mask substrate may comprise one or more patterns of light-blocking regions and light-transmitting regions. In some variations, the mask substrate may have a predetermined set of patterns, where the number of patterns may correspond to the number of data acquisition time points in an acquisition time window or frame. In the context of low-coherence interferometry or UOT, the number of predetermined mask patterns or configurations may correspond with the number of predetermined phase shifts of a reference light signal. In some variations, a mask substrate may have a single pattern that remains constant or static during speckle image acquisition. Light-blocking regions may be regions of the mask substrate that completely obstructs or greatly attenuates the transmission of light, so that detector pixels located under light-blocking regions of a mask receive few (if any) photons of a speckle image (for instance). For example, light-blocking regions may comprise structures or materials that optically absorb or reflect all (or nearly all) incoming light so that little (if any) light is incident on the detector pixels under those regions. Light-transmitting regions may be regions of the mask substrate that allow for the unimpeded transmission of light, so that detector pixels located under light-transmitting regions of the mask receive the photons of a speckle image (for instance). For example, light-transmitting regions may comprise structures or materials that are optically transparent such that incoming light is transmitted through the mask to the detector pixels under those regions. The size, shape, and arrangement of the light-transmitting and light-blocking regions may be changed or adjusted in a temporally precise manner, and in some variations, in synchrony with a light source (e.g., a light source of an interferometry system). The light source may be a high-coherence source, a low-coherence source, a pulsed source (e.g., with microsecond, nanosecond, picosecond, femtosecond, etc. pulse width), or a continuous wave source. Examples of a light source may include a super luminescent diode (SLD), a light emitting diode (LED), a Ti:Saph laser, a white light lamp, a diode-pumped solid-state (DPSS) laser, a laser diode (LD), a light emitting diode (LED), a super luminescent light emitting diode (sLED), a titanium sapphire laser, and/or a micro light emitting diode (mLED), among other light sources. The wavelength(s) of light generated by a light source may vary between about 350 nm to about 1.5 um, and/or may be UV light, visible light, and/or near-infrared and infrared light. The light source may generate monochromatic light comprising single-wavelength light, or light having multiple wavelengths (e.g., white light). In some variations, a light source can emit a broad optical spectrum or emit a narrow optical spectrum that is then rapidly swept (e.g., changed over time) to functionally mimic or create an effective broad optical spectrum. The size, shape, and arrangement of the light-transmitting and light-blocking regions may be determined at least in part based on the number of light data acquisition time points in an acquisition window (which may correspond to number of predetermined phase shifts of the reference light in a set), image feature size (e.g., speckle grain size), size of the imager light sensor and/or detector pixel array, and to the extent that the pattern comprises repeating light-transmitting and light-blocking regions, the spatial frequency of the pattern may depend on the combination of the number of acquisition time points and image feature size. FIGS. 2B and 2C depict example variations of optical mask patterns (i.e., patterns on a substrate of a mask or mask substrate patterns).

FIG. 2B depicts one variation of a mask substrate pattern (220) comprising a plurality of light-transmitting regions (222) and a plurality of light-blocking regions (224) in the form of stripes with different widths, where the proportion of the total mask substrate (e.g., mask substrate area and/or width) occupied by light-transmitting stripes is about 10%. This mask substrate pattern may be used with, for example, an imaging system where image data is acquired at 10 time points in an acquisition window. In the context of low-coherence interferometry or UOT, this pattern (220) may be used for the acquisition of interference patterns or speckle images that correspond to 10 predetermined phase shifts of the reference light signal. Mask substrate pattern (220) may be one in a set of 10 patterns where the light-transmitting stripes are shifted laterally by the width of a stripe. For the mask pattern (220), each light-transmitting stripe (222) of width $S_w$ is separated by a distance of $9*S_w$, such that there is one light-transmitting stripe (222) for every nine light-blocking stripes (224) (i.e., a ratio of a width of a light-transmitting stripe (222) to a width of a light-blocking stripe (224) of 1:9, also referred to as a width ratio). The mask substrate pattern (220) may be specific to the type of measurement being performed. For example, if a time-series analysis of 10 images is desired, for example, a 1:9 mask may be used to recorded 10 time-series images on to one frame of the imager sensor. In this example, each image may have 1/10 the amount of data (i.e., 90% speckle image data is blocked by the mask device), but this may be compensated for by using a high-pixel-count imager sensor.

FIG. 2C depicts another variation of a mask substrate pattern (230) comprising a plurality of light-transmitting regions (232) and a plurality of light-blocking regions (234) in the form of stripes with the same (or similar) width, where the proportion of the total mask substrate (e.g., mask substrate area and/or width) occupied by light-transmitting stripes is about 50%. For the mask pattern (230), each light-transmitting stripe (232) of width $S_w$ is separated by a distance of $S_w$, such that there is one light-transmitting stripe (232) for every light-blocking stripe (234) (i.e., a width ratio of a width of a light-transmitting stripe to a width of a light-blocking stripe of 1:1). This pattern may be used with, for example, an imaging system where image data is acquired at two time points in an acquisition window. In the context of low-coherence interferometry or UOT, this pattern (230) may be used for the acquisition of interference patterns or speckle images that correspond to 2 predetermined phase shifts of the reference light signal. Mask substrate pattern (230) may be one in a set of two patterns where the light-transmitting stripes are shifted laterally by the width of a stripe.

Figure 2D:
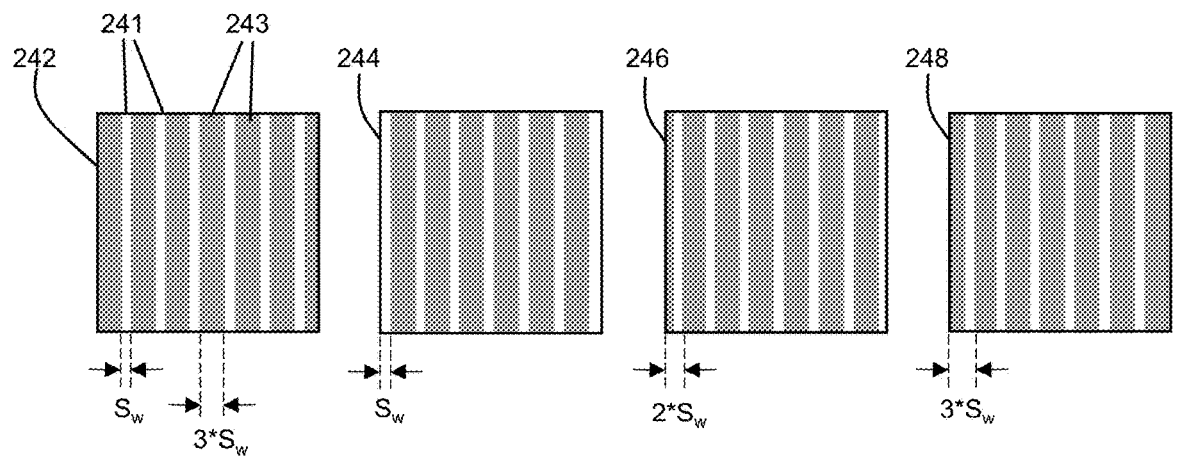
FIG. 2D depicts a set of four predetermined mask substrate patterns or configurations.
Figure 2E:
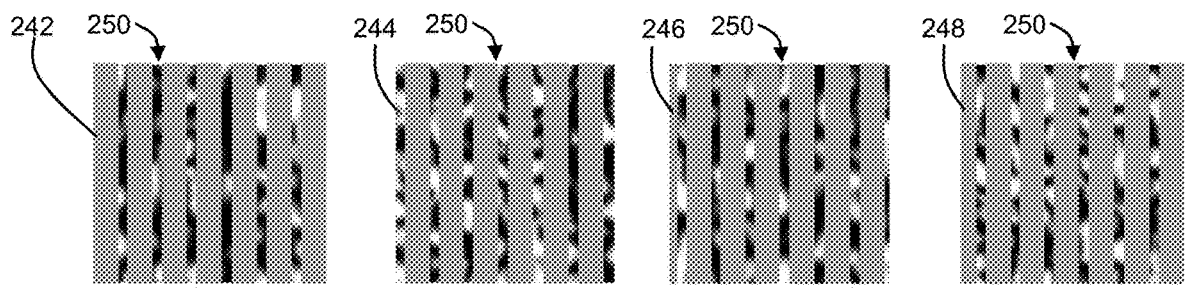
FIG. 2E depicts the mask substrate patterns of FIG. 2D disposed over an image sensor for detecting four interference patterns or speckle images.
Figure 2F:
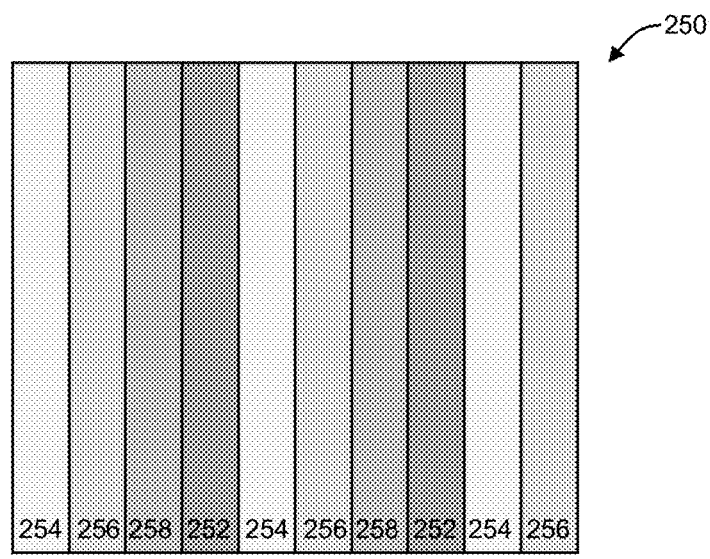
FIG. 2F is a schematic representation of a subset of the image sensor detector pixels that correspond with the light-transmitting regions of the mask substrate patterns of FIG. 2D.

FIG. 2D depicts a series of four predetermined mask substrate configurations or mask substrate patterns (242, 244, 246, 248) comprising a plurality of light-transmitting regions (241) and a plurality of light-blocking regions (243) in the form of stripes, where the proportion of the total mask substrate (e.g., mask substrate area and/or width) occupied by light-transmitting stripes is about 25%. For each of the predetermined mask patterns depicted in FIG. 2D, each light-transmitting stripe (241) of width $S_w$ is separated by a distance of $3*S_w$, such that there is one light-transmitting stripe (241) for every light-blocking stripe (243) that has a width of $3*S_w$ or three light-blocking stripes having a width of $S_w$ (i.e., a width ratio of a width of a light-transmitting stripe to a width of a light-blocking stripe of 1:3). This pattern may be used with, for example, an imaging system where image data is acquired at four time points in an acquisition window. In the context of low-coherence interferometry or UOT, the first mask substrate pattern (242) may be used for the acquisition of a first interference pattern or speckle image that corresponds to a first predetermined phase shift of the reference light signal, the second mask substrate pattern (244) may be used for the acquisition of a second interference pattern or speckle image that corresponds to a second predetermined phase shift of the reference light signal, the third mask substrate pattern (246) may be used for the acquisition of a third interference pattern or speckle image that corresponds to a third predetermined phase shift of the reference light signal, and the fourth mask substrate pattern (248) may be used for the acquisition of a fourth interference pattern or speckle image that corresponds to a fourth predetermined phase shift of the reference light signal. The widths of the light-transmitting and light-blocking stripes of each of the mask substrate patterns may be the same, but may be spatially shifted laterally by a multiple of the width of a stripe $S_w$ (e.g., $S_w$, $2*S_w$, $3*S_w$). The four mask substrate patterns may be created using an array of electrically-tunable optical structures. Alternatively, these four substrate patterns may be mimicked with a single substrate pattern having a width ratio of light-transmitting to light-blocking stripes of 1:3, and shifting or moving the single substrate pattern across the light sensor region of the imager in steps, with step intervals that are the same size as (or approximately the same size as) the stripe width $S_w$. In the context of low-coherence interferometry or UOT, such patterns may be used for the acquisition of interference patterns or speckle images that correspond to four predetermined phase shifts of the reference light signal. For example, the mask substrate may be adjusted to a first pattern before a first light pulse or data acquisition time point, and then adjusted to a second pattern before a second light source or data acquisition time point. FIG. 2E depicts the mask substrate configurations or patterns (242, 244, 246, 248) disposed over an image sensor (250) as the image sensor acquires four interference patterns or speckle images (for example, each interference pattern may arise from combining the sample light pattern (light that has interacted with tissue) with a reference beam (light that has not interacted with tissue) having different relative phase shifts). An image sensor may comprise a plurality of detector pixels in an array, and the different mask substrate configurations may expose certain detector pixels (e.g., the detector pixel regions located under the light-transmitting portions of the mask substrate configuration or pattern) to acquire image data. The image data acquired for each of the four mask substrate configurations may be combined in a manner similar to that depicted in FIG. 1B to form a composite image. FIG. 2F depicts the image sensor (250) and the regions or sets of detector pixels that are located under light-transmitting regions of the mask substrate configurations or patterns in FIG. 2D. As schematically represented in FIG. 2F, a first set of detector pixels (252) comprising stripes of detector pixels located under the light-transmitting stripes/regions of the first mask substrate pattern or configuration (242), a second set of detector pixels (254) comprising stripes of detector pixels located under the light-transmitting stripes/regions of the second mask substrate pattern or configuration (244), a third set of detector pixels (256) comprising stripes of detector pixels located under the light-transmitting stripes/regions of the third mask substrate pattern or configuration (246), and a fourth set of detector pixels (258) comprising stripes of detector pixels located under the light-transmitting stripes/regions of the fourth mask substrate pattern or configuration (248).

The proportion or percentage of light-transmitting regions of a mask pattern over the total area of the substrate may be determined by the number (X) of images to be acquired by the imaging system during an acquisition time window (e.g., less than or equal to the acquisition time for a frame of data of the imager sensor, less than a speckle decorrelation time interval, from about 5 μs to about 100 μs, about 10 μs, about 20 μs, about 40 μs, about 50 μs, about 100 μs, from about 500 μs to about 1 ms, about 800 μs, about 1 ms, etc.), and may be (100/X) %. For example, for X=2 (which may simulate a 2-bin lock-in camera), a mask pattern may have a 50% fill-factor (i.e., a mask pattern where about 50% the area of the substrate is occupied by one or more light-blocking regions), and for X=4 (which may simulate a 4-bin lock-in camera), a mask pattern may have a 75% fill-factor (i.e., a mask pattern where about 75% the area of the substrate is occupied by one or more light-blocking regions and 25% of the area of the substrate is occupied by one or more light-transmitting regions). The width of a stripe (or dimension of any pattern feature) may be determined at least in part by an image feature size, such as the size of a speckle grain, and/or the number of images to be captured in the acquisition time window (e.g., less than the acquisition time for a frame of data of the imager sensor, less than a speckle decorrelation time interval, from about 5 μs to about 100 μs, about 10 μs, about 20 μs, about 40 μs, about 50 μs, about 100 μs, from about 500 μs to about 1 ms, about 800 μs, about 1 ms, etc.). The number of light-blocking stripes may be determined by dividing the area corresponding to the desired fill-factor by a dimension (e.g., width) of a speckle grain and/or detector pixel. In some variations, the mask substrate may be subdivided into stripes or checks of arbitrary dimensions, and a set of X mask patterns for acquiring X number of images during an acquisition time window may be determined by selecting a portion of the stripes or checks to be light-transmitting (e.g., in proportion to X) for each mask pattern, where each stripe or check is a light-transmitting region for only one mask pattern. While the mask patterns described above and depicted in FIGS. 2B and 2C comprise stripes with uniform width repeated with uniform spacing, it should be understood that the patterns may comprise stripes with non-uniform or variable widths separated by non-uniform spacing, as long as the proportion of light-transmitting regions of the mask pattern corresponds with the number of images captured by the imaging system during an acquisition time window as described above. In still other mask pattern variations, patterns may comprise an array of checks (i.e., similar to a checkerboard) where the light-transmitting regions and light-blocking regions may be interspersed throughout the array. The density of light-transmitting regions for some mask patterns may be increased in regions of the image where higher levels of resolution may be desired (e.g., where high-contrast and/or high-variable image features are expected).

Some optical mask devices may comprise substrates that are configured to vary the pattern of light-transmitting and light-blocking regions by adjusting or tuning the optical characteristics of certain regions of the substrate, which can change the location of the light-transmitting and light-blocking regions relative to the imager sensor without moving the mask device with respect to the imager sensor. For example, an optical mask device may comprise an electronically-controlled mask substrate where the optical properties of the substrate may be spatially modulated, for example, based on absorption, retroreflection, transmission or other optical properties. In this matter, a mask substrate may be able to change between at least two or more mask patterns. Alternatively or additionally, the pattern on the substrate may not change, but the locations of the light-transmitting and light-blocking regions of the mask device relative to the imager sensor may be changed by moving the mask device and/or imager sensor ("dynamic sensor"). A "dynamic mask" may refer to a movable mask and/or to a mask with dynamically adjustable or tunable optical properties. The range of motion may be predetermined and on the order of several detector pixels, for example, approximately the size (e.g., width) of a speckle grain, and/or an integer number of detector pixels. In some systems, the mask pattern may change in conjunction with relative motion between the mask device and the imager sensor during image acquisition.

One variation of a mask device comprising a substrate that is configured to change mask patterns may comprise an array of optical structures with electrically-tunable optical properties. The optical structures may be tuned to have the optical properties for a particular or predetermined mask patterns based on mask configuration data transmitted from the imaging system controller to the mask. The area of the array of optical structures may correspond with the area of the light-sensing region of the imager sensor (e.g., approximately the area of the detector pixel area of the imager sensor). In some variations, the optical structures may be electrically controllable optical modulators such as quantum well heterostructures (e.g., with graded or stepped barriers), and/or other semiconductor heterostructures with electrically tunable optical properties and high bandwidths of control, e.g., at MHz rates, and/or high-speed liquid crystal based transmission modulators, and/or digital micro-mirror device (DMD), and/or other micro-electro-mechanical systems (MEMS) based tunable/controllable reflector systems, and/or multi-layer LCD systems. In variations where a mask substrate comprises an array of tunable optical structures, these optical structures may be tiled into alternating rows or columns where even rows or columns are controlled by a first control signal and odd rows or columns are controlled by a second control signal, where the first and second control signals may be from the mask device electronic circuitry and may be derived from command signals from the imaging system controller (e.g., mask configuration data). It should be understood that the control signal(s), such as mask configuration signals, may be routed to the array of optical structures in any appropriate fashion such that the predetermined mask patterns are replicated on the substrate in accordance with the timing parameters set by the imaging system controller (e.g., predetermined mask patterns $m_0, m_1, m_2, \ldots, m_X$ for corresponding acquisition time points $t_0, t_1, t_2, \ldots, t_X$ which may, in the context of low-coherence interferometry or UOT correspond with a predetermined reference light signal phase shifts $p_0, p_0, p_0, \ldots, p_X$ and so forth).

Figure 2G:
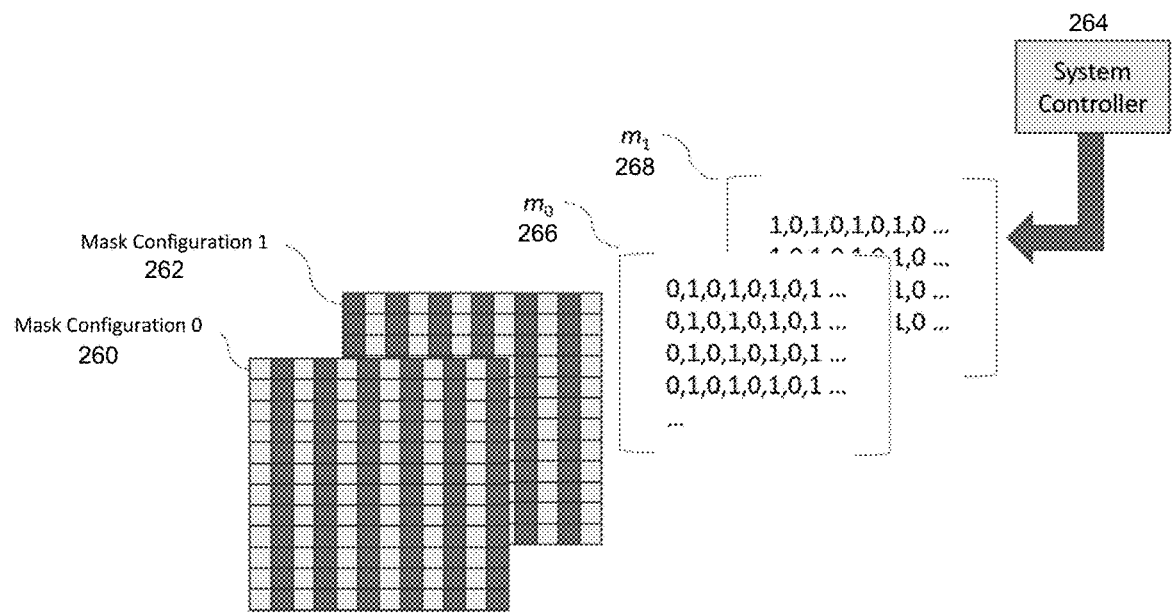
FIGS. 2G and 2H are schematic depictions of different mask substrate patterns or configurations and corresponding mask configuration signals.
Figure 2H:
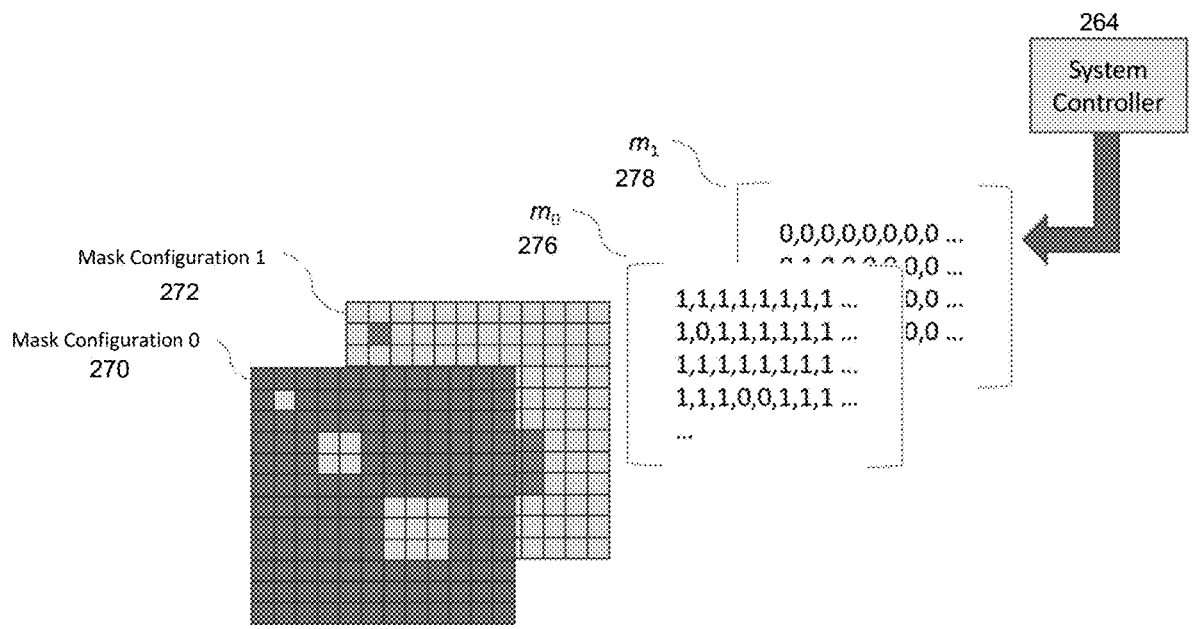

In one variation, a system controller in communication with a mask device substrate comprising an array of optical structures with electrically-tunable optical properties may comprise a plurality of mask configuration signal channels (e.g., ports, data bus, wires, fibers, etc.), where the number of mask configuration signal channels correspond with the number of optical structures in the mask substrate. For example, if a mask substrate comprises 64 optical structures, the system controller may comprise 64 mask configuration signal channels, where the signal on each channel drives the optical properties of a single optical structure. One example of mask configuration signals that may be used to control electrically-tunable optical structures of a mask substrate to have certain mask patterns or configurations is schematically depicted in FIGS. 2G and 2H. FIG. 2G depicts two mask substrate configurations or patterns (260, 262) for a mask substrate comprising an array of 144 electrically-tunable optical structures. The system controller (264) may be connected to the mask device and/or mask substrate via 144 mask configuration signal channels, where each channel is mapped to an optical structure of the array. To attain the first mask substrate pattern or configuration (260) on the mask substrate, the system controller (264) may generate 144 mask configuration signals (266) that are transmitted over the mask configuration signal channels to the mask substrate, where a signal value of "1" may indicate a high level of opacity (e.g., light-blocking) and a signal value of "0" may indicate a low level of opacity (e.g., light-transmitting). To attain the second mask substrate pattern or configuration (262) on the mask substrate, the system controller (264) may generate 144 mask configuration signals (268) that are transmitted over the mask configuration signal channels to the mask substrate, where an optical element that had a low level of opacity (e.g., light-transmitting) in the first mask substrate pattern or configuration now has a high level of opacity (e.g., light-blocking) in the second substrate mask pattern or configuration.

A variety of mask substrate patterns or configurations may be attained by adjusting the mask configuration signals. FIG. 2H depicts a different set of predetermined mask substrate patterns (260, 262) for a mask substrate comprising an array of 144 electrically-tunable optical structures. The system controller (264) may be connected to the mask device and/or mask substrate via 144 mask configuration signal channels, as described above. To attain the third mask substrate pattern or configuration (270) on the mask substrate, the system controller (264) may generate 144 mask configuration signals (276) that are transmitted over the mask configuration signal channels to the mask substrate, and to attain the fourth mask substrate pattern or configuration (272) on the mask substrate, the system controller (264) may generate 144 mask configuration signals (278) that are transmitted over the mask configuration signal channels to the mask substrate. In other variations, there may be more than two mask patterns or configurations (e.g., 3, 4, 5, 6, etc.) for any arbitrary-sized array of optical structures, and such patterns or configurations may be encoded in the mask configuration signals as described above.

Alternatively or additionally, the pattern on a mask device may be static (e.g., where optical characteristics of electrically-tunable optical structures are maintained or kept the same, where the substrate comprises materials or coatings arranged in a predetermined pattern that cannot be optically tuned), but the mask device may be mechanically moved (e.g., stepped) relative to the imager sensor to predetermined positions corresponding to predetermined acquisition time points (that may correspond with a predetermined set of reference light signal phase shifts) in an acquisition time window (e.g., which may be less than or equal to the acquisition time for a frame of data of the imager sensor, less than a speckle decorrelation time interval, from about 5 µs to about 100 µs, about 10 µs, about 20 µs, about 40 µs, about 50 µs, about 100 µs, from about 500 µs to about 1 ms, about 800 µs, about 1 ms, etc.). In some variations, the pattern of light-transmitting and light-blocking regions on the mask substrate may comprise a pattern of light-transmitting and light-blocking coatings, inks, materials deposited on the substrate. For example, light-transmitting regions may comprise any light-transmissive materials such as glass, acrylic, and/or quartz glass, and may optionally include anti-glare coatings. Light-blocking regions may comprise any light-absorbing or light-reflecting materials such as paints, carbon nanotube coatings, and/or black coatings such as black foil or polymer (e.g., black coatings and/or coated black foils manufactured by ACKTAR LTD, Kiryat-Gat, Israel). By moving or stepping the mask device across the imager sensor, the light-transmitting and light-blocking regions on the mask are disposed over different sets of detector pixels at each acquisition time point. A mask device position sensor may provide real-time data as to the position of the mask device to the imaging system controller so that the motion of the mask device can be adjusted accordingly. Alternatively or additionally, the imager sensor may be mechanically moved (e.g., stepped) relative to the mask device to predetermined positions corresponding to predetermined acquisition time points (that may correspond with a predetermined set of reference light signal phase shifts) in an acquisition time window (e.g., which may be less than or equal to the acquisition time for a frame of data of the imager sensor, less than a speckle decorrelation time interval, from about 5 µs to about 100 µs, about 10 µs, about 20 µs, about 40 µs, about 50 µs, about 100 µs, from about 500 µs to about 1 ms, about 800 µs, about 1 ms, etc.). The mechanical displacements of the mask device and/or imager sensor may be from about 2 µm to about 10 µm, and may in some variations depend on the detector pixel size of the imager sensor. The substrate may comprise one or more actuators, which may or may not be integrated with the attachment structure. Similarly, the imager sensor may be coupled to one or more actuators. In some variations, the substrate and/or imager sensor may be attached to a mount that is coupled to the actuator, which moves the mount to predetermined locations. Examples of actuators for moving the mask device and/or imager sensor may include piezoelectric positioners or materials, and/or piezo actuators such as PLOXX PICMA® chip actuators (miniature multilayer piezo actuators by Physik Instrumente, Sausalito, Calif.) having sub-nanometer resolution, mechanical resonances greater than or equal to about 600 kHz. Multiple piezo actuators may be arranged in series for larger ranges of motion. Motion of the imager sensor and/or mask device may optionally be combined with electrically tuning the optical characteristics of the mask substrate (i.e., adjusting the location, size, and/or shape of light-transmitting and light-blocking regions). The location of the input speckle may also be synchronized with electronically controlled mask opening or configuration change. For example, a light-blocking region of a mask substrate disposed over one or more detector pixels may transition to a light-transmitting region of the mask substrate (either by mechanically moving the mask or electronically changing the optical property of the portion of the substrate disposed over the one or more detector pixels) when a speckle image has a desired alignment with the one or more detector pixels. That is, the light from a speckle image is blocked when the one or more detector pixels and/or mask device are not aligned (e.g., centered) with respect to speckles in the image, and the light from the speckle image impinges on (i.e., is transmitted through the mask device substrate onto) the one or more detector pixels when the desired alignment is attained. Alternatively or additionally, the optical mask configuration (e.g., relative position of the light-transmitting and light-blocking regions on the mask device relative to the detector pixels of the imager, mask substrate pattern, relative mask and imager sensor position) may be synchronized with the pulsing or strobing of a light source. For example, a change in the mask substrate configuration may be synchronized with a light source pulse. This may expand the ability of the imaging system to further tune or adjust light that is incident on every detector pixel of the imager sensor, and/or to tune or adjust the detection timing of a speckle grain at a detector pixel.

In the context of imaging a speckle pattern emerging from a scattering medium, to perform UOT, low-coherence interferometry or any wavefront measurement for phase conjugation, it may be desirable to move the imager sensor relative to the mask device (i.e., keeping the mask device stationary), especially if an imager sensor was selected with a detector pixel size that approximates the speckle size. An imager sensor with detector pixels that are similar in size to the anticipated speckle grain size may help increase speckle efficiency. This may allow half of all speckles within the field of view of the imager to be measured, leading to ~N/2 speckles captured where N is the number of detector pixels, whereas other approaches may achieve N/X speckles captured where X is the number of speckle patterns or images to be acquired during an acquisition time window, and in some variations may be greater than or equal to 2 (e.g., 3, 4, 5, 6, 7, 8, 9, 10, etc.). Increasing the number of speckles measured in wavefront measurements schemes such as UOT or low-coherence interferometry because shot noise in the measurement can be suppressed or reduced by averaging over many distinct speckles, and similarly increasing the number of speckles measured is important in wavefront measurement for digital phase conjugation or wavefront modification. Obtaining measurements that include an increased number of speckles across a speckle image may facilitate the generation of a phase conjugated wavefront that more precisely approximates (e.g., by having more optical modes) the wavefront of the light detected by the detector pixels. If the mask is moved instead of the imager sensor, a speckle grain may be blocked from impinging on the imager if it does not follow or track a light-transmitting region of the mask. Alternatively, the speckle size may be increased (e.g., doubled to be approximately twice the size as the detector pixels) such that the speckle may be detected by one or more detector pixels in a light-transmitting region of the mask.

In some variations, an imager may comprise an array of detector pixels that may be activatable by groups (e.g., rows, columns, clusters of rows or columns) so that predetermined groups of detector pixels are acquiring image data at corresponding acquisition time points. For example, the imager circuitry may be configured to apply control voltages to specific detector pixels or groups of detector pixels (e.g., one or more rows and/or columns of detector pixels), which may transiently enable or disable the ability of the detector pixel to detect photons. A bias voltage may be applied to photodiodes contained in each detector pixel such that the detector pixel does or does not generate a photo-current depending on the applied bias voltage. The activation of certain groups or sets of detector pixels (e.g., via one or more bias voltages) may be controlled by the imaging system controller, which may store predetermined detector pixel activation patterns corresponding to each data acquisition time point in a controller member, and transmit command signals to the imager to activate the appropriate detector pixels.

The imaging system controller may be in communication with the optical mask device, and the imager (including imager sensor). The controller may also be in communication with one or more actuators (as applicable) that are coupled to the mask device and/or imager sensor. In the context of a low-coherence interferometry or UOT system, the imaging system controller may also be in communication with an interferometer (e.g., sample light source), and/or an acoustic assembly configured to deliver ultrasound into the tissue. Optionally, the imaging system controller may be in communication with an acousto-optic modulator. For example, the controller may transmit one or more synchronization signals to the interferometer, and/or acoustic assembly, as well as the optical mask device and imager in order to ensure that image data is acquired at time points that correspond with changes in the sample light and/or ultrasound pulses that are emitted to the tissue. With a common sync or trigger signal across the various subcomponents of the imaging system, the acquired data may be analyzed according to the parameters (e.g., phase shift, frequency shift, light intensities, etc.) of the light and/or ultrasound pulses emitted into the tissue. For example, the optical mask device may comprise an input port that receives synchronization and/or mask substrate configuration signals from that controller and an output port that transmits detector pixel array data (e.g., light intensities) to the controller for analysis. By synchronizing across these subcomponents, the controller can decode and analyze the data from each detector pixel based on the mask configuration, reference light phase value, and/or ultrasound frequency tag to extract speckle data for each acquisition time point.

In some variations, the controller may be configured to calibrate the relative positions of the optical mask device and the imager sensor. One variation of a calibration method or protocol may comprise illuminating the entire optical mask device substrate area and imager sensor area (e.g., full-field illumination), changing the configuration of the optical mask device to each of the predetermined mask configurations (e.g., mechanically moving the imager sensor and/or mask device, adjusting the optical characteristics of various regions of the mask substrate) while acquiring a frame of image data for each mask configuration, and identifying any detector pixel regions in the acquired image data frames that have been illuminated in two mask configurations. This may indicate areas of overlap between light-transmitting regions in two mask configurations. The actuator and/or electrical control signals to the substrate may be adjusted to eliminate these overlaps.

Figure 3A:
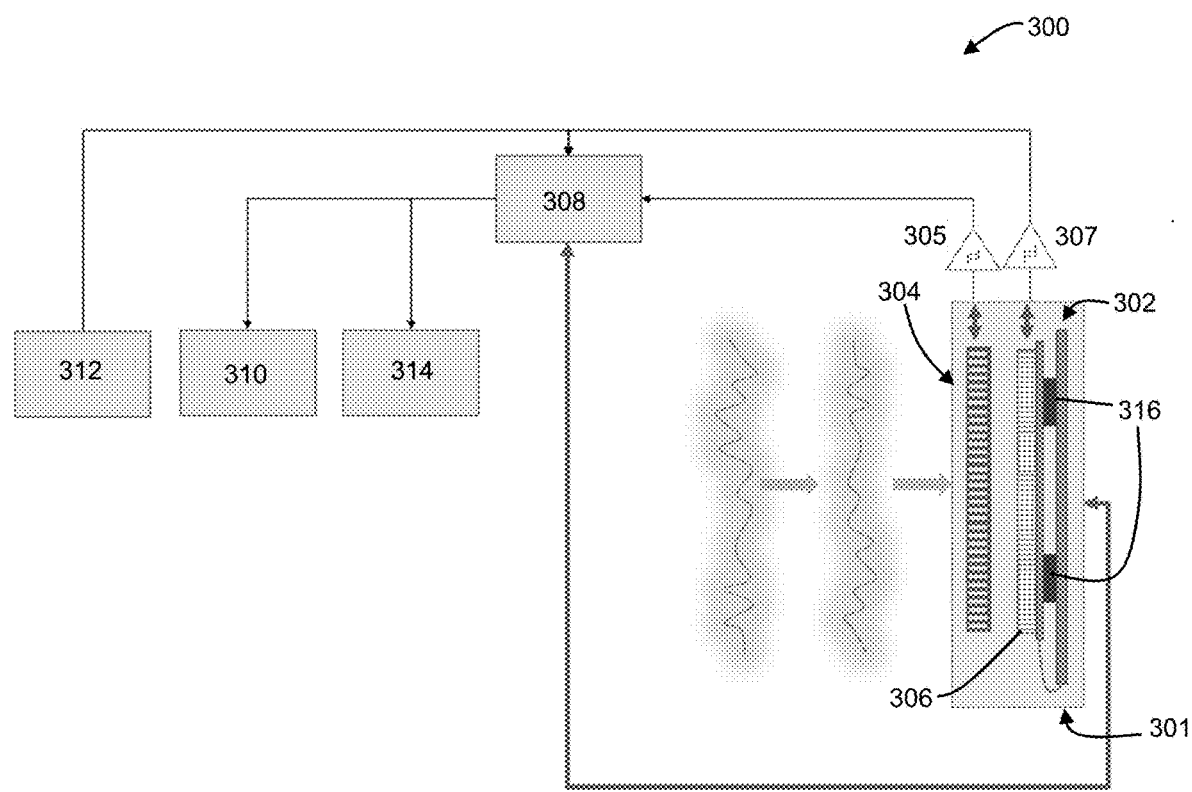
FIG. 3A is a schematic representation of one variation of an imaging system comprising an optical mask device.

FIG. 3A depicts one variation of an imaging system (300) comprising an imager (302), an optical mask device (304) disposed over the imager sensor (306) and a system controller (308) in communication with the imager and the optical mask device. In some variations, the imager (302) and the optical mask device (304) may be enclosed in a common housing as an imager assembly (301). A low-coherence interferometry imaging system may comprise an interferometer including a sample light source (e.g., laser (310)), and an UOT imaging system may further comprise an optoacoustic modulator (312) and an ultrasound generator (314). The light source (310) may be configured to emit light pulses into sample tissue (e.g., skin surface on the head near a brain region of interest). The light source may be a high-coherence source, a low-coherence source, a pulsed source (e.g., with microsecond, nanosecond, picosecond, femtosecond, etc. pulse width), or a continuous wave source. Examples of a light source may include a super luminescent diode (SLD), a light emitting diode (LED), a Ti:Saph laser, a white light lamp, a diode-pumped solid-state (DPSS) laser, a laser diode (LD), a light emitting diode (LED), a super luminescent light emitting diode (sLED), a titanium sapphire laser, and/or a micro light emitting diode (mLED), among other light sources. The wavelength(s) of light generated by a light source may vary between about 350 nm to about 1.5 um, and/or may be UV light, visible light, and/or near-infrared and infrared light. The light source may generate monochromatic light comprising single-wavelength light, or light having multiple wavelengths (e.g., white light). In some variations, a light source can emit a broad optical spectrum or emit a narrow optical spectrum that is then rapidly swept (e.g., changed over time) to functionally mimic or create an effective broad optical spectrum. The ultrasound generator (314) may be configured to emit ultrasound pulses and/or waves into the sample tissue, in synchrony with the light source, as coordinated by the system controller. The system (300) may also comprise one or more actuators (316), which may be piezo actuators as described previously, coupled to the imager sensor (306) and configured to move the sensor with respect to the mask device. The optical mask device (304) may comprise a mask position sensor (305), and the imager sensor may be coupled to a position sensor (307). As described previously, the mask device may be coupled to actuators configured to move the mask device relate to the imager sensor. In some variations, the mask device and/or the imager sensor may be moved and held at the predetermined position before a data acquisition time point, which may help reduce or prevent blurring due to the moving sensor and/or mask device. For example, the light source (310) may be synchronized with the ultrasound at predetermined data acquisition time points that occur after motion of the sensor and/or mask have ceased.

Figure 3B:
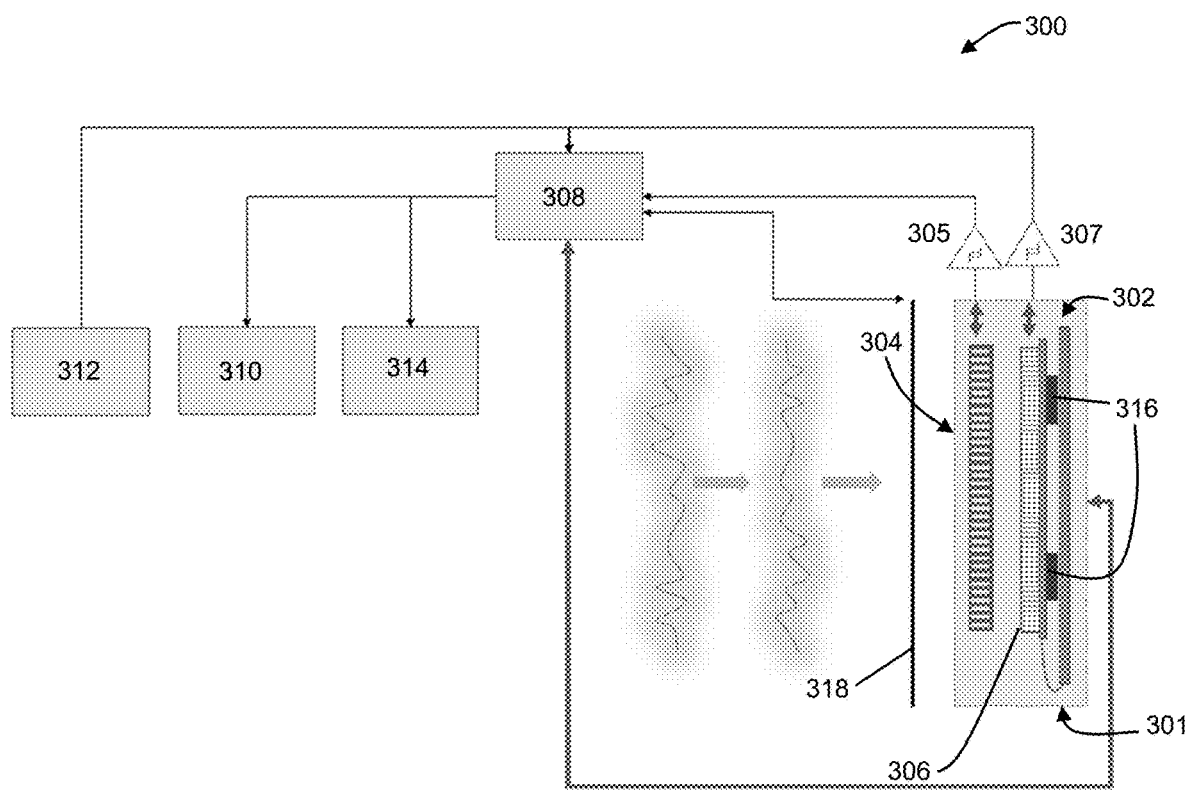
FIG. 3B is a schematic representation of another variation of an imaging system comprising an optical mask device.

FIG. 3B depicts an imaging system similar to the system of FIG. 3A, further comprising a shutter (e.g., motorized shutter, solenoid shutter, rotor drive shutter, stepper motor shutter, electronic shutter, acousto-optical modulator, electro-optic modulator, electrically controllable retroreflector, liquid crystal based modulator, polarization based modulator, etc.), chopper or other light blocking component (318). Closing the shutter or chopper (318) during mask pattern reconfiguration and/or mask device motion and/or detector sensor motion may help to reduce image blurring. The system controller (308) may receive image data acquired by the imager sensor and timing data associated with the image data (e.g., a time stamp representing the absolute time of image data acquisition, timing data representing relative time of image data acquisition relative to other imaging system components). The system controller (308) may also coordinate the timing of the light source (310) pulses, ultrasound (314) pulses, mask configuration (e.g., pattern and/or position relative to the sensor), imager sensor position relative to the mask, and/or sensor acquisition timing to help alleviate or reduce blur artifacts and/or phase drifts. For example, the controller may coordinate the timing of the motion of the mask device and/or imager sensor so that their relative motion is not driven at a resonant frequency. Optionally, some imaging systems may comprise one or more vibration isolation mounts or pads coupled to any components in the optical path to help reduce unwanted vibrations and/or path length changes. This may help to reduce or eliminate any phase drift that may occur due to relative motion of mask and sensor, since phase drifts may result in unwanted blurring or mixing of speckle patterns between adjacent detector pixel columns on the imager sensor. In some variations, the system controller may phase-lock the sensor/mask motion to the emission of sample light pulses from the light source (e.g., any of the light sources described above), and in the case of UOT, ultrasound pulse emission. In addition, since the ultrasound waves or pulses are slower than light waves, the system controller may trigger the ultrasound source based on a trigger signal that occurs earlier than the light source trigger signal.

Figure 4A:
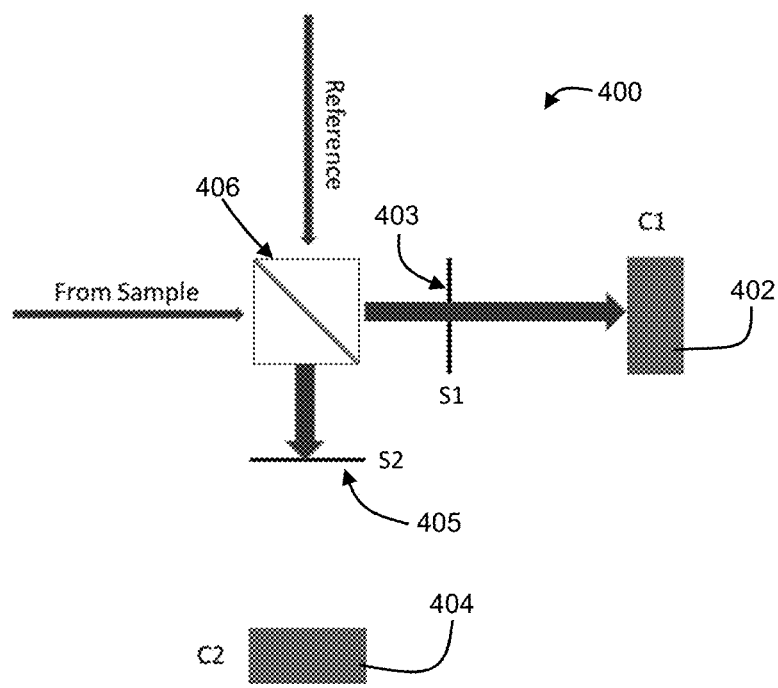
FIG. 4A is a schematic representation of one variation of an imaging system comprising an two imager sensors.
Figure 4B:
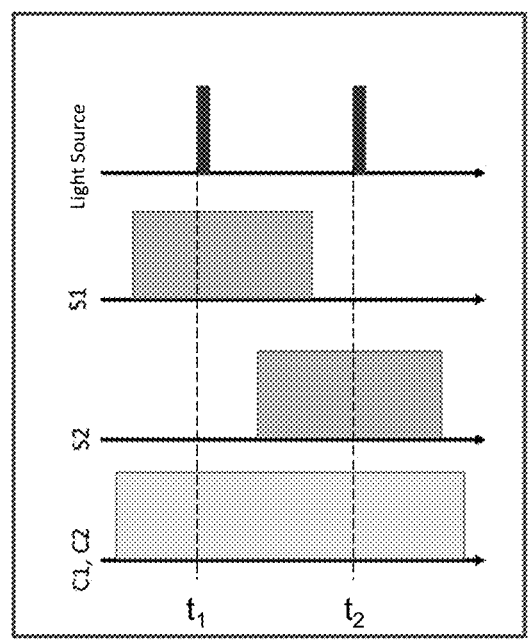
FIG. 4B is a timing diagram associated with the use of the system of FIG. 4A.

In some variations, an optical mask device may be used to create a lock-in camera effect using two or more imager sensors rather than one imager sensor. In this variation, a set of imager sensors arranged such that each of the detector pixels of one sensor is aligned with the corresponding detector pixels of the other sensors (i.e., arranged in an OLIC-like system that comprises a plurality of separate imagers that are optically aligned with each other, such that any given pixel(s) on the imagers have a known one-to-one correspondence with each other). One variation of such an imaging system is schematically depicted in FIG. 4A. The imaging system (400) may comprise a first imager C1 having a first imager sensor (402), a second imager C2 having a second imager sensor (404), a beam splitter (406) that directs light (e.g., from a tissue sample) to both the first and second imagers C1 and C2, a first optical mask device (403) disposed in the optical path between the splitter (406) and the first imager C1, and a second optical mask device (405) disposed in the optical path between the splitter (406) and the second imager C2. The first and second optical mask devices may have two mask configurations, the first light-blocking configuration comprising a mask pattern where the entire area of the substrate over the light-detecting region of the imager is light-blocking and the second light-transmitting configuration comprising a mask pattern where the entire area of the substrate over the light-detecting region of the imager is light-transmitting. In some variations, the first and second optical mask devices may comprise a shutter, which may include optical choppers, electronic shutters, optical modulators, liquid-crystal shutters, retroreflectors, or any other means of transiently blocking light clocked with an external control signal. The timing between a light source (i.e., that emits a sample light pulse to tissue) and the optical mask devices (403, 405) may allow the two imagers C1 and C2 to capture time-dependent changes of the speckle pattern with arbitrary control limited only by the speed of the optical mask devices (403, 405). The two imager sensors (402, 404) may be aligned pixel-by-pixel so as to measure the same input speckle pattern in an OLIC-like scheme. Then, through the use of the two timed optical mask devices (which timing may be coordinated by the image system controller in accordance with, for example, with the timing diagram of FIG. 4B), a first image is captured at time-point $t_1$ on the first sensor and then a second image is captured subsequently at a second time-point $t_2$ on the second sensor. As shown in FIG. 4B, the first optical mask device (403, S1) is in the light-transmitting configuration prior to the first light source pulse at time-point $t_1$, and the second optical mask device (405, S2) is in the light-blocking configuration at time-point $t_1$. Although in this example the first and second imagers are continuously activated, only the first imager (402) acquires any image data in this configuration because only the first optical mask device (403, S1) is in the light-transmitting configuration. After the first light source pulse, the first optical mask device (403, S1) is transitioned to the light-blocking configuration and the second optical mask device (405, S2) is transitioned to the light-transmitting configuration. At time-point $t_2$, the second optical mask device (405, S2) is in the light-transmitting configuration while the first optical mask device (403, S1) is in the light-blocking configuration, allowing the second imager (405) to acquire image data. FIG. 4A depicts the configuration at time-point $t_1$, where the first optical mask device (403) is in the light-transmitting configuration (e.g., shutter is open) and the second optical mask device (405) is in the light-blocking configuration (e.g., shutter is closed). In some variations, a first light source pulse may be used to create a first interference or speckle pattern detected by the first imager at the first time point, and a second light source pulse may be used to create a second interference or speckle pattern detected by the second imager at the second time point. This is in contrast with other systems (e.g., an OLIC system) that uses a single light source pulse to generate an interference or speckle pattern that is measured by both imagers. For example, in a system comprising a laser light source, two short laser pulses each having a pulse width on the order of a few nanoseconds may be used to generate interference patterns, rather than a single long laser pulse having a width on the order of microseconds.

Methods

An imaging system comprising an imager with a conventional imager sensor (i.e., each detector pixel having a single electronic data bin storing a single intensity value) and an optical mask device disposed over the imager sensor may be used in a variety of imaging contexts with different imaging modalities. In some variations, the imaging systems described herein may be used in non-invasive optical brain imaging. One example of non-invasive brain imaging comprises the detection of ballistic and/or quasi-ballistic photons using a low-coherence interferometry imaging system where the reference light is rapidly stepped through a predetermined set of phase shifts (e.g., X phase shifts) that gives rise to a corresponding set of interference or speckle light patterns (i.e., X interference light patterns). Detection of ballistic photons (e.g., photons that have a path length that match the reference path length) and quasi-ballistic photons (e.g., photons that have a path length that approximates the reference path length within the coherence length of the light source) may help to generate images of deep tissue structures and functional activities at higher resolution as compared to traditional diffuse optical tomography methods. The set of phase shifts to the reference light may be applied in a time frame shorter than a speckle decorrelation time interval (e.g., about 1 ms or less, 100 µs or less), generating X interference or speckle patterns within that short time frame. An imaging system comprising an optical mask device with X patterns or configurations of light-transmitting and light-blocking regions (such as any described above), may partition the detector pixel array of the imager sensor into X sets of detector pixels, where each set of the X sets of detector pixels is allocated for the acquisition of one of the X interference patterns. This may simulate the function of a X-bin lock-in camera. By acquiring image data for the X interference patterns within the speckle decorrelation time interval, background light signals can be subtracted from the overall intensity calculation, leaving an intensity value or number of ballistic and/or quasi-ballistic photons that have been emitted from the brain matter of interest. The intensity value of ballistic and/or quasi-ballistic photons may represent a physiological parameter of interest, for example, blood perfusion or flow rate to the brain matter of interest. Additional details regarding the detection of quasi-ballistic and/or ballistic photons using a low-coherence interferometry imaging system may be found in U.S. Non-Provisional patent application Ser. No. 15/853,538, filed Dec. 22, 2017 and U.S. patent application Ser. No. 15/853,209, filed Dec. 22, 2017, each of which is hereby incorporated by reference in its entirety.

Figure 5A:
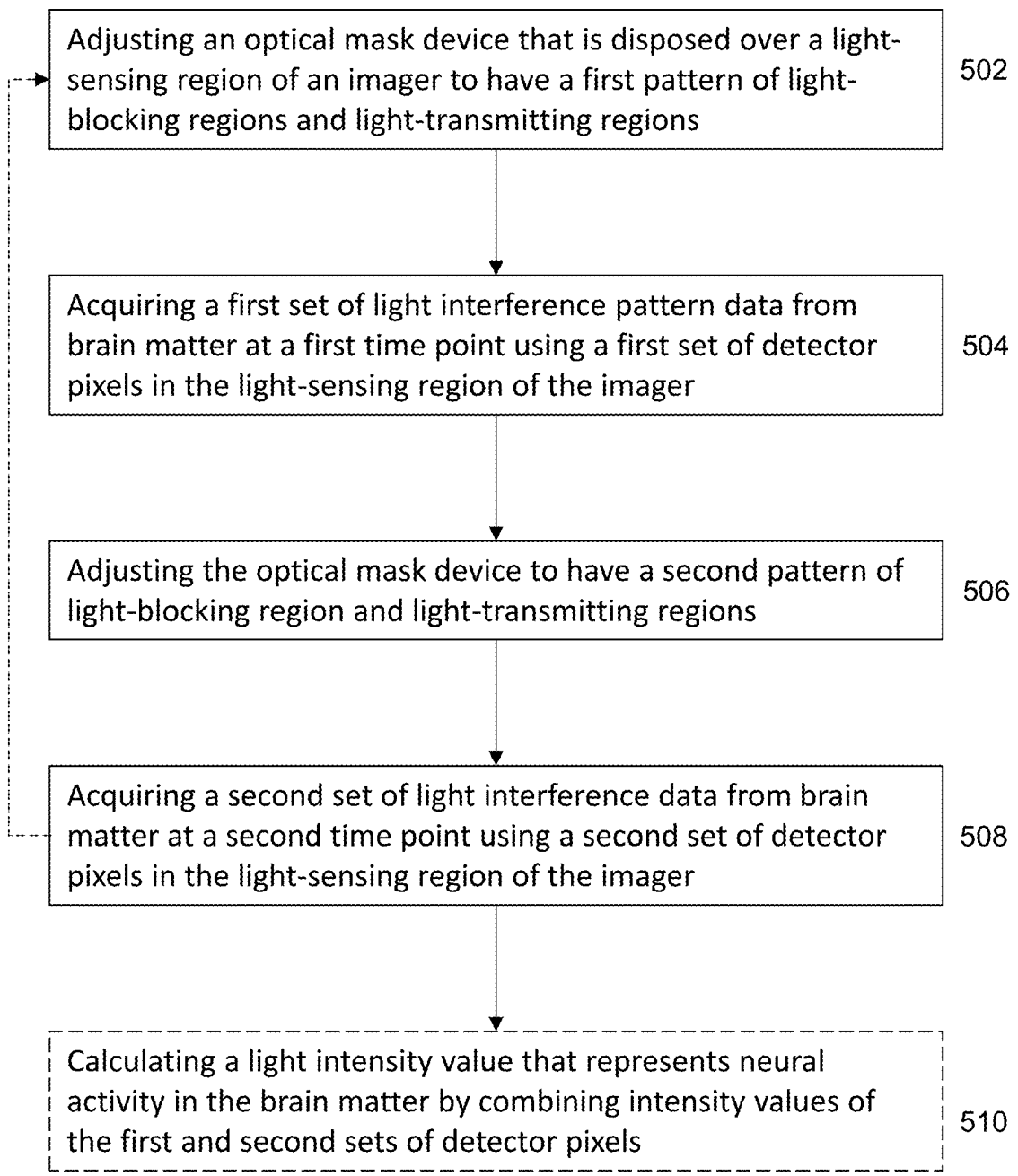
FIG. 5A is a flowchart depiction of one variation of a method for non-invasive optical detection of neural activity.

FIG. 5A depicts one variation of a method for non-invasive optical detection of neural activity. Method (500) may comprise adjusting (502) an optical mask device that is disposed over a light-sensing region of an imager to have a first pattern of light-blocking regions and light-transmitting regions, acquiring (504) a first set of light interference pattern data from brain matter at a first time point using a first set of detector pixels in the light-sensing region of the imager, adjusting (506) the optical mask device to have a second pattern of light-blocking region and light-transmitting regions, acquiring (508) a second set of light interference data from brain matter at a second time point using a second set of detector pixels in the light-sensing region of the imager, and calculating (510) a light intensity value (e.g., a cumulative light intensity value) that represents neural activity in the brain matter by combining (e.g., by averaging, and/or calculating a quadrature quantity, and/or taking a difference between two intensity values, and/or taking an absolute value of a difference between intensity values, normalizing intensity values, etc.) intensity values of the first and second sets of detector pixels. For example, in the context of acquiring speckle image data in an interferometry system (e.g., low-coherence interferometry for the detection of quasi-ballistic and/or ballistic photons, UOT, OCT, etc.), combining light intensity data from the first and second sets of detector pixels may comprise calculating the absolute difference of the intensity value of a first detector pixel in the first set with the intensity value of a second detector pixel in the second set that corresponds to the same speckle in the speckle image ($diff_0$), calculating this absolute difference of intensity values over all such corresponding pixel pairs between the first and second sets of detector pixels (i.e., calculating $diff_0$, $diff_1$, $diff_2$, . . . , $diff_Y$, where Y is the number of pixels in each set of detector pixels) and then averaging the these values to derive a cumulative intensity value (i.e., cumulative intensity value is $$\frac{1}{Y}\sum_{i=0}^{Y} diff_i).$$

The difference in intensity values recorded by a first detector pixel and a corresponding second detector pixel may represent the intensity changes of a single speckle over two time points, where the intensity changes in that speckle may be due to shifting phases in a reference light signal and/or light source, and/or changes in neural activity. For example, the first and second mask patterns (e.g., first and second substrate configurations) may be used to acquire light interference data from first and second phase shifts of the reference light signal. In a variation where four sets of light interference pattern data (e.g., speckle image data) are acquired over four sets of detector pixels using four mask substrate patterns or configurations, combining intensity values of four sets of detector pixels may comprise calculating a quadrature quantity of the intensity values of four individual detector pixels, where each detector pixel is measuring the intensity of the same speckle (i.e., recording the intensity changes of the speckle over four time points). Alternatively or additionally, intensity values of the different sets of detector pixels may be combined by taking a difference between intensity values, and/or taking an absolute value of a difference between intensity values, normalizing intensity values, etc. of two or more detector pixels in two different sets. The combination of intensity values over multiple sets of detector pixels that represent changes in light intensity of an interference pattern over time may be used to derive a cumulative light intensity value or quantity that represents neural activity and/or physiological activity over time (e.g., deoxygenated and/or oxygenated hemoglobin concentration, water concentration, and/or electrical and/or synaptic activity, etc.) at the brain matter of interest. The steps (502-508) of the method (500) may be performed within a speckle decorrelation time interval, and may optionally be repeated for third and fourth mask patterns (e.g., third and fourth substrate configurations) to acquire light interference data from third and fourth phase shifts of the reference light signal (where all four phase shifts occur within the speckle decorrelation time interval). Method (500) may optionally comprise calculating a cumulative intensity value over four intensity values may comprise methods and principles of quadrature detection, and similarly averaged over all the pixels in each set of detector pixels. For example, the sample light may be stepped through there may be two phase shifts, where the first phase may be 0 and the second phase may be $\pi$, or may be stepped through four phase shifts, where the phase values may be 0, $\pi/2$, $\pi$, and $3\pi/2$.

FIG. 5B depicts another variation of a method for non-invasive optical detection of neural activity using an imaging system with an optical mask device disposed over a detector pixel array of a conventional imager. Method (520) may comprise adjusting (522) positions of light-blocking and light transmitting region of an optical mask device at a predetermined number (X) of time points to a plurality of predetermined positions that correspond with (or in synchrony with) a predetermined number of phases of a reference light signal, acquiring (524) light interference data for each of the plurality of predetermined positions using the detector pixel array, and calculating (526) a plurality (X) of light intensity values corresponding to the number (X) of phases of the reference light signal, wherein changes in the plurality of light intensity values over time represent neural activity. Calculating a plurality of light intensity values may comprise averaging (or otherwise combining) imager detector pixel values for each of the predetermined number of time points.

For ultrasound modulated optical tomography (UOT) and low-coherence interferometry for the detection of quasi-ballistic and/or ballistic photons, through heterodyne parallel speckle detection, ultrasound-tagged light may be differentiated from the reference light signal (i.e., light from the light source that is not emitted to the brain tissue) and untagged light in a speckle image. This may be attained by isolating the interference term that contains a contribution from the tagged light while subtracting away other interference terms, which can be attained, for example, by phase-shifting holography. A conventional imager and an optical mask device (such as any of the mask devices described herein) can attain this acquiring by subtracting the intensity data acquired using a second mask (intensitydata2) from the intensity data acquiring using a first mask (intensitydata1) in the case where there are two phase shifts, or by (intensitydata4−intensitydata2)$^2$+(intensitydata3−intensitydata1)$^2$, i.e., quadrature implementation, in the case where there are four phase shifts. In one implementation, each interference pattern is presented to the sensor at a different time and with a different relative phase shift between the reference beam (light that has not interacted with tissue) and the sample light pattern (light that has interacted with tissue). These phase shifts and interference patterns are acquired within the speckle decorrelation time interval for a decorrelating tissue scattering medium. Alternatively, an oscillating heterodyne interference term that represents a combination of the different frequencies of the different light signals that combine to form an interference pattern (e.g., a sum or difference of frequencies $f_1$ and $f_2$, where $f_1$ is a frequency of a first light interference pattern and $f_2$ is a frequency of a second light interference pattern) can be detected by sampling at 2× or 4× the beat frequency (e.g., 2×, 3×, 5×, 6×, etc. the beat frequency) using a conventional imager and the mask configuration described above, and performing similar calculations.

In a non-limiting UOT example, a 1 MHz ultrasound pulse in the sample may be used to shift the base optical frequency of light by 1 MHz. There is also a reference (with per-pixel power denoted $P_{ref}$) light source that is shifted by 2 MHz, and untagged light at the base frequency. The total measurement takes 1 μs. In the first half of the process (e.g., a first 500 ns), the light-transmitting regions of the mask pattern may allow a speckle pattern to fall on all the "odd" detector pixel columns of the imager sensor while the "even" detector pixel columns are located under light-blocking regions of the pattern. At the 500 ns time point, the sensor may be shifted by one detector pixel column width, to allow the speckle pattern to fall on the "even" detector pixel columns of the sensor. After another 500 ns the measurement is completed, and alternating columns of interference image data have been obtained.

In the formulas below, unknown$_1$, unknown$_2$, unknown$_3$ indicate the unknown relative wavefront phases of the light arriving at the detector pixel due to the scattering medium (e.g., brain tissue). These are different for each detector pixel due to the randomness of the speckle interference (as well as rapidly changing due to decorrelation), as are the intensities of the $P_{untagged}$ and $P_{tagged}$. Instantaneous intensity on particular pixel, $P_{1,1}=$ $P_{ref}+P_{untagged}+P_{tagged}+2*\text{sqrt}(P_{reference}*P_{tagged})*\cos$
$(2\pi*1\text{ MHz}*\text{time}+\text{unknown}_1)$ $$2*\text{sqrt}(P_{reference}*P_{untagged})*\cos(2\pi*2 \text{ MHz}*\text{time}+\text{unknown}_2)$$

$$2*\text{sqrt}(P_{untagged}*P_{tagged})*\cos(2\pi*1 \text{ MHz}*\text{time}+\text{unknown}_3)$$

The measured charge on detector pixel $P_{1,1}$ may be proportional to the integral of the above equation in the time between 0 and 500 ns the measured intensity of the detector pixel is, given that the product of the untagged and reference light integrates to close to zero, $$500 \text{ ns}*[P_{ref}+P_{untagged}+P_{tagged}]+\text{sqrt}(P_{reference}*P_{tagged})*[-2\sin(\text{unknown}_1)]/(2\pi*1 \text{ MHz})+\text{sqrt}(P_{untagged}*P_{tagged})*[-2\sin(\text{unknown}_3)]/(2\pi*1 \text{ MHz})$$

The second part of the image may be captured during the time from 500 ns to 1 μs which is assigned to the neighboring column for a specific pixel, $P_{1,2}$. Measured intensity on a particular pixel following the integration is $P_{1,2}=$ $$500 \text{ ns}*[P_{ref}+P_{untagged}+P_{tagged}]+\text{sqrt}(P_{reference}*P_{tagged})*[2\sin(\text{unknown}_1)]/(2\pi*1 \text{ MHz})+\text{sqrt}(P_{untagged}*P_{tagged})*[2\sin(\text{unknown}_3)]/(2\pi*1 \text{ MHz})$$

By taking the absolute difference $|P_{1,1}-P_{1,2}|$, the DC background terms $P_{ref}+P_{untagged}+P_{tagged}$ may be removed:

$$|4*\text{sqrt}(P_{reference}*P_{tagged})*[\sin(\text{unknown}_1)]+4*\text{sqrt}(P_{untagged}*P_{tagged})*[\sin(\text{unknown}_3)]|/(2\pi*1 \text{ MHz})$$

By summing or averaging these absolute differences, of neighboring column values at each row, across the entire imager sensor and assuming that $P_{reference}$ and $P_{untagged}$ are relatively static over time, the resulting single value may be linear with $P_{tagged}$, and may represent a physiological optical parameter (e.g., level of deoxygenated and/or oxygenated hemoglobin concentration of relative abundance, level of water concentration or relative water concentration).

Although particular embodiments of the present inventions have been shown and described, it will be understood that it is not intended to limit the present inventions to the disclosed embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

The invention claimed is:

1. A system for non-invasive optical detection of neural activity comprising:
an imager having a light-sensing region;
an optical mask device configured to be disposed over the light-sensing region of an imager;
a beam splitter configured to
split a light beam into a sample light signal and a reference light signal, and
direct the sample light signal to a tissue sample of an anatomical structure and the reference light signal along a light path that does not interact with the tissue sample of the anatomical structure, the reference light signal configured to cycle through a plurality of phases; and
a controller configured to
adjust the optical mask device to have a first pattern of light-blocking regions and light-transmitting regions,
direct the imager to acquire, while the optical mask has the first pattern of light-blocking regions and light-transmitting regions and while the reference light signal has a first phase included in the plurality of phases, a first set of light interference pattern data from the tissue sample at a first time point using a first set of detector pixels in the light-sensing region of the imager, the first light interference pattern data comprising a combination of the reference light signal having the first phase and the sample light signal after the sample light signal interacts with the tissue sample,
adjust the optical mask device to have a second pattern of light-blocking regions and light-transmitting regions,
direct the imager to acquire, while the optical mask has the second pattern of light-blocking regions and light-transmitting regions and while the reference light signal has a second phase included in the plurality of phases, a second set of light interference data from the tissue sample at a second time point using a second set of detector pixels in the light-sensing region of the imager, the second light interference pattern data comprising a combination of the reference light signal having the second phase and the sample light signal after the sample light signal interacts with the tissue sample, and
calculate a first light intensity value by combining intensity values of each detector pixel in the first set of detector pixels and calculating a second light intensity value by combining intensity values of each detector pixel in the second set of detector pixels;
wherein a combination of the first light intensity value and the second light intensity value represents the neural activity.

2. The system of claim 1, wherein the detector pixels in the second set are different from the detector pixels in the first set.

3. The system of claim 1, wherein the first phase is 0 and the second phase is π.

4. The system of claim 1, wherein the controller is further configured to determine a physiological optical parameter of the tissue sample based on the first and second light intensity values.

5. The system of 1, wherein the controller is further configured to:
adjust the optical mask to have a third pattern of light-blocking regions and light-transmitting regions;
direct the imager to acquire, while the optical mask has the third pattern of light-blocking regions and light-transmitting regions and while the reference light signal has a third phase included in the plurality of phases, a third set of light interference data from the tissue sample at a third time point using a third set of detector pixels in the light-sensing region of the imager, wherein the third light interference pattern data comprises a combination of the reference light signal having the third phase and the sample light signal after the sample light signal interacts with the tissue sample;
adjust the optical mask to have a fourth pattern of light-blocking regions and light-transmitting regions;
direct the imager to acquire, while the optical mask has the fourth pattern of light-blocking regions and light-transmitting regions and while the reference light signal has a fourth phase included in the plurality of phases, a fourth set of light interference data from the tissue sample at a fourth time point using a fourth set of detector pixels in the light-sensing region of the imager, wherein the fourth light interference pattern data comprises a combination of the reference light signal having the fourth phase and the sample light signal after the sample light signal interacts with the tissue sample; and calculate a third light intensity value by combining intensity values of each detector pixel in the third set of detector pixels and calculating a fourth light intensity value by combining intensity values of each detector pixel in the fourth set of detector pixels.

6. The system of claim 5, wherein:

the first phase is 0, the second phase is $\pi/2$, the third phase is $\pi$, and the fourth phase is $3\pi/2$; and the controller is further configured to determine a physiological optical parameter of the tissue sample based on the first, second, third, and fourth light intensity values.

7. A system for non-invasive optical measurement of neural activity comprising:

an optical splitter configured to split a light beam into a sample light signal and a reference light signal, and direct the sample light signal to a tissue sample of an anatomical structure and the reference light signal along a light path that does not interact with the tissue sample of the anatomical structure, the reference light signal configured to cycle through a predetermined number (N) of phases; and a controller configured to adjust positions of light-blocking and light-transmitting regions of an optical mask at a predetermined number (X) of time points to a plurality of predetermined positions that correspond with the predetermined number (N) of phases of the reference light signal, wherein the optical mask is disposed over a detector pixel array of an imager, direct the imager to acquire light interference data for each of the plurality of predetermined positions using the detector pixel array, and calculate a plurality (X) of light intensity values corresponding to the predetermined number (N) of phases of the reference light signal by averaging imager detector pixel values for each of the predetermined number (X) of time points, wherein changes in the plurality of light intensity values over time represent neural activity.

* * * * *